US012638429B2

(12) United States Patent
Maki et al.

(10) Patent No.: US 12,638,429 B2
(45) Date of Patent: May 26, 2026

(54) GAS SENSOR

(71) Applicant: NGK INSULATORS, LTD., Nagoya (JP)

(72) Inventors: Shintaro Maki, Nagoya (JP); Kota Katagiri, Nagoya (JP); Kohei Yaita, Nagoya (JP); Yuya Seike, Nagoya (JP); Satoru Shiraishi, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 259 days.

(21) Appl. No.: 18/609,516

(22) Filed: Mar. 19, 2024

(65) Prior Publication Data

US 2024/0319154 A1     Sep. 26, 2024

(30) Foreign Application Priority Data

Mar. 23, 2023     (JP) ................................. 2023-046514

(51) Int. Cl.
    *G01N 33/00*     (2006.01)
    *G01D 11/24*     (2006.01)
    *G01D 11/26*     (2006.01)

(52) U.S. Cl.
    CPC ....... *G01N 33/0037* (2013.01); *G01D 11/245* (2013.01); *G01D 11/26* (2013.01)

(58) Field of Classification Search
    CPC ........... G01N 33/0037; G01N 33/0009; G01D 11/245; G01D 11/26
    See application file for complete search history.

(56) References Cited

U.S. PATENT DOCUMENTS

| | | | | |
|---|---|---|---|---|
| 2010/0050740 A1* | 3/2010 | Matsubara | ......... | G01N 27/4077 |
| | | | | 73/23.31 |
| 2013/0312485 A1* | 11/2013 | Yonezu | .............. | G01N 27/4078 |
| | | | | 73/23.2 |
| 2015/0260698 A1* | 9/2015 | Hirata | ................ | G01N 27/4078 |
| | | | | 73/23.31 |

FOREIGN PATENT DOCUMENTS

JP          2015-172515 A     10/2015

* cited by examiner

*Primary Examiner* — Thomas M Hammond, III
(74) *Attorney, Agent, or Firm* — MATTINGLY & MALUR, PC

(57)     ABSTRACT

A possibility is suppressed that a gripping position of a gripping member is moved by an external impact and a gripping force is reduced. In a gas sensor according to one aspect of the present invention, a gripping member that grips a portion covered with a tube in an outer peripheral surface of a cylindrical body such that the tube protrudes to a side opposite to an open end of the cylindrical body grips an outer peripheral surface covered with the tube of a caulked portion closest to the open end among one or more caulked portions formed in the cylindrical body.

6 Claims, 5 Drawing Sheets

FIG. 1

FRONT END SIDE ← → REAR END SIDE

GAS SENSOR 1

FIG. 3

FRONT END SIDE ◄──► REAR END SIDE 431 (2)

STRESS CONCENTRATION IS ALLEVIATED 4312    4311
(2)    B (2)

STRESS CONCENTRATION 4312    4311
(2)    B (2)

70

GAS SENSOR

CROSS-REFERENCE TO RELATED APPLICATION

The present application claims priority from Japanese application JP 2023-046514, filed on Mar. 23, 2023, the contents of which is hereby incorporated by reference into this application.

FIELD OF INVENTION

The present invention relates to a gas sensor.

BACKGROUND

Conventionally, there has been known a gas sensor that detects a concentration of a specific gas such as oxygen or $NO_x$ in a gas to be measured such as an exhaust gas of an automobile. For example, JP 2015-172515 A below has disclosed a gas sensor including: a cylindrical body in which a sensor element is disposed thereinside and an open end is formed; a lead wire that is electrically connected to the sensor element and extends outward from the inside of the cylindrical body through the open end; a tube that covers an outer peripheral surface of an end portion of the cylindrical body including the open end and a portion of the lead wire extending outward from the open end; and a gripping member that grips a portion of an outer peripheral surface covered with the tube of the cylindrical body such that the tube protrudes to a side opposite to the open end. In the gas sensor disclosed in JP 2015-172515 A, a caulked portion caulked in a radially reduced shape is formed on an open end side of the cylindrical body.

SUMMARY OF INVENTION

The present inventors have found the following problems in a conventional gas sensor disclosed in JP 2015-172515 A or the like. That is, the present inventors have found a problem that a gripping force of the gripping member may be reduced when a gripping position of the gripping member moves in an axial direction of the gas sensor due to an external impact.

FIG. 5 is enlarged cross-sectional views each schematically showing a main part of a conventional gas sensor CS. Specifically, FIG. 5 shows details of the open end side (hereinafter, also referred to as a "rear end side") of the conventional gas sensor CS. In FIG. 5, a right-left direction in the drawing is an axial direction (a longitudinal direction) of the conventional gas sensor CS, and a left side in the drawing is a front end side and a right side in the drawing is the rear end side. As illustrated in FIG. 5, the conventional gas sensor CS has an axis and is configured to extend along the longitudinal direction (the axial direction), and has a front end and a rear end as respective ends in the longitudinal direction. One end in the longitudinal direction is the front end, and another end is the rear end. In an example of FIG. 5, the conventional gas sensor CS is disposed such that the front end of the conventional gas sensor CS faces a left direction and the rear end of the conventional gas sensor CS faces a right direction.

As illustrated in FIG. 5, in the conventional gas sensor CS, caulked portions 431 each caulked in a radially reduced shape are formed on the rear end side of a cylindrical body 40. In the example shown in FIG. 5, the two caulked portions 431 are formed on the rear end side of the cylindrical body

40, and specifically, a caulked portion 431(1) and a caulked portion 431(2) are formed. In description below, when it is not necessary to distinguish the caulked portion 431(1) and the caulked portion 431(2) from each other, they may be simply described as the "caulked portion(s) 431". In addition, when the plurality of caulked portions 431 are distinguished from each other, "(1)", "(2)", "(3)", ... , "(n)", and "(n+1)" are added after the member number "431" to distinguish each of the plurality of caulked portions. "n" is an integer of "1" or more.

In the conventional gas sensor CS having such a configuration, as illustrated in FIG. 5, a gripping member 10 may grip an outer peripheral surface covered with a tube 70 of the cylindrical body 40, that is, an outer peripheral surface of a crest portion 439. The crest portion 439 is a portion other than a portion where the caulked portions 431 is formed on the rear end side of the cylindrical body 40, and can also be regarded as a portion where the caulked portion 431 is not formed. In the example shown in FIG. 5, the crest portion 439 is a portion between the caulked portion 431(1) and the caulked portion 431(2) in the axial direction.

The present inventors have found that a problem below may occur when the gripping member 10 grips the outer peripheral surface of the crest portion 439 of the cylindrical body 40 in the conventional gas sensor CS. That is, a problem has been found that a gripping force of the gripping member 10 may be reduced when a gripping position of the gripping member 10 is moved in the axial direction by an external impact, in particular, when the gripping position is moved from the outer peripheral surface of the crest portion 439 to an outer peripheral surface of the caulked portion 431 as illustrated in FIG. 5.

The present invention has been made in view of such a circumstance in one aspect, and an object of the present invention is to provide a gas sensor in which a possibility that a gripping position of a gripping member is moved by an external impact and a gripping force is reduced is suppressed.

In order to solve the above-described problem, the present invention adopts a configuration below.

A gas sensor according to a first aspect includes: a sensor element; a cylindrical body in which the sensor element is disposed thereinside and an open end is formed; a lead wire that is electrically connected to the sensor element and extends outward from the inside of the cylindrical body through the open end; a tube that covers an outer peripheral surface of an end portion of the cylindrical body including the open end and a portion of the lead wire extending outward from the open end; and a gripping member that grips a portion covered with the tube in an outer peripheral surface of the cylindrical body such that the tube protrudes to a side opposite to the open end, wherein on a side of the cylindrical body where the open end is formed, one or more caulked portions are formed, each of the caulked portions including: two inclined portions in each of which a diameter of the cylindrical body continuously changes along an axial direction of the cylindrical body; and a bottom portion disposed between the two inclined portions in the axial direction and having a constant diameter of the cylindrical body along the axial direction, the gripping member grips an outer peripheral surface of the caulked portion closest to the open end in the axial direction among the one or more caulked portions, the outer peripheral surface being covered with the tube, and in each of the two inclined portions included in the caulked portion gripped by the gripping member, (A) or (B) is 30° or more and less than 90°, where (A) is an angle between the inclined portion and a plane obtained by extending the bottom portion toward a side of the inclined portion, and (B) is an angle between a plane parallel to a tangent of the inclined portion at a contact point between the inclined portion and the bottom portion, and the plane obtained by extending the bottom portion toward the side of the inclined portion.

With this configuration, in the gas sensor, the gripping member grips the outer peripheral surface covered with the tube of the caulked portion closest to the open end in the axial direction (hereinafter, also referred to as a "rear end-side caulked portion") among the one or more caulked portions. That is, unlike the gripping member of the conventional gas sensor CS that grips the "portion of the cylindrical body covered with the tube where the caulked portion is not formed", the gripping member of the gas sensor grips the outer peripheral surface covered with the tube of the rear end-side caulked portion. The present inventors conducted an experiment, and confirmed that the gripping member that grips the outer peripheral surface covered with the tube of the rear end-side caulked portion is less likely to move even when an impact is applied, as compared with the gripping member of the conventional gas sensor. Therefore, the gas sensor exerts an effect that the possibility can suppressed that the position (the gripping position) of the gripping member is moved by an external impact and the gripping force of the gripping member is reduced.

In addition, in the gas sensor, the angle between the inclined portion and the bottom portion in the rear end-side caulked portion satisfies the following condition. That is, the angle of (A) or the angle of (B) is 30° or more and less than 90°.

The present inventors further conducted an experiment to identify a desirable range of the angle of each of the inclined portions of the rear end-side caulked portion. As a result, it has been confirmed that when the inclined portion has a tapered shape, that is, when the inclined portion is formed so as to have a straight line in a cross section parallel to the longitudinal axis of the gas sensor (the axis of the cylindrical body) and in contact with the axis, the angle of the inclined portion is desirably within a range below. That is, the present inventors have confirmed that it is desirable to set the angle (hereinafter, also referred to as an "angle α") between the inclined portion and the plane obtained by extending the bottom portion toward the side of the inclined portion to 30° or more. In addition, since the inclined portion is a portion where the diameter of the cylindrical body continuously changes along the axial direction of the cylindrical body, the angle α is less than 90°.

In addition, the present inventors have confirmed that when the inclined portion has a rounded shape, that is, when the inclined portion is formed so as to have a curved line in the cross section parallel to and in contact with the axis, it is desirable to set the angle of the inclined portion within the range below. That is, the present inventors have confirmed that it is desirable to set the angle between the plane parallel to the tangent of the inclined portion at the contact point between the inclined portion and the bottom portion and the plane obtained by extending the bottom portion toward the side of the inclined portion (hereinafter, also referred to as an "angle β") to 30° or more. In addition, similarly to the angle α, the angle β is also less than 90°.

The present inventors have experimentally confirmed that when the inclined portion has a tapered shape, the gripping position of the gripping member can be reliably fixed by the inclined portion by setting the angle α to 30° or more and less than 90°. In addition, the present inventors have experimentally confirmed that when the inclined portion has a rounded shape, the gripping position of the gripping member can be reliably fixed by the inclined portion by setting the angle β to 30° or more and less than 90°. When each of the angle α and the angle β is set to less than 30°, the position of the gripping member (gripping position) cannot be reliably fixed by the inclined portion of the rear end-side caulked portion, and the gripping position of the gripping member is easily moved (easily displaced) by an external impact, and the gripping force is reduced.

Therefore, the gas sensor exerts an effect below by setting the angle α (that is, the angle of (A)) to 30° or more and less than 90° or setting the angle β (that is, the angle of (B)) to 30° or more and less than 90° in the inclined portion. That is, the gas sensor exerts the effect of reliably fixing the gripping position of the gripping member by the inclined portion of the rear end-side caulked portion.

With a gas sensor according to a second aspect, in the gas sensor according to the first aspect, an axial length of the gripping member may be equal to or less than an axial length of the caulked portion gripped by the gripping member. With this configuration, in the gas sensor, the axial length of the gripping member is equal to or less than the axial length of the caulked portion gripped by the gripping member. The present inventors have studied a relationship that the axial length of the gripping member and the axial length of the caulked portion gripped by the gripping member (that is, the rear end-side caulked portion) should satisfy. The present inventors have experimentally confirmed that the gripping force of the gripping member can be improved by setting the axial length of the gripping member to be equal to or less than the axial length of the rear end-side caulked portion. Therefore, by setting the axial length of the gripping member to be equal to or less than the axial length of the rear end-side caulked portion, the gas sensor exerts an effect that the gripping force of the gripping member can be improved.

With a gas sensor according to a third aspect, in the gas sensor according to the first or second aspect, a diameter of a portion of the cylindrical body where the caulked portion is not formed may be larger by 0.5 mm or more than a diameter of the cylindrical body at the bottom portion of the caulked portion gripped by the gripping member.

With this configuration, in the gas sensor, the diameter of the portion of the cylindrical body where the caulked portion is not formed is larger by 0.5 mm or more than the diameter of the cylindrical body at the bottom portion of the caulked portion gripped by the gripping member. That is, in the gas sensor, the diameter of the portion of the cylindrical body where the caulked portion is not formed is larger by 0.5 mm or more than the diameter of the cylindrical body at the bottom portion of the rear end-side caulked portion.

When a difference in the diameter of the cylindrical body is small between the portion where the caulked portion is not formed and the bottom portion of the rear end-side caulked portion, for example, when the bottom portion of the rear end-side caulked portion is not sufficiently deeper than the portion where the caulked portion is not formed, a problem below may occur. That is, the gripping position of the gripping member cannot be reliably fixed by the rear end-side caulked portion, the gripping position of the gripping member is easily moved by an external impact, and the gripping force of the gripping member may be reduced. By making the bottom portion of the rear end-side caulked portion sufficiently deeper than the portion where the caulked portion is not formed, the gripping position of the gripping member can be reliably fixed by the rear end-side caulked portion, and the movement of the gripping position and the reduction in the gripping force can be prevented. Specifically, by making the bottom portion of the rear end-side caulked portion deeper by 0.5 mm or more than the portion where the caulked portion is not formed, the gripping position of the gripping member can be reliably fixed by the rear end-side caulked portion, and the movement of the gripping position and the reduction in the gripping force can be prevented.

Therefore, the diameter of the portion of the cylindrical body where the caulked portion is not formed is made larger by 0.5 mm or more than the diameter of the cylindrical body at the bottom portion of the rear end-side caulked portion, by which the gas sensor exerts an effect below. That is, the gas sensor exerts the effect that the gripping position of the gripping member can be reliably fixed by the rear end-side caulked portion, and that the movement of the gripping position and the reduction in the gripping force of the gripping member can be prevented.

With a gas sensor according to a fourth aspect, in the gas sensor according to any of the first to third aspects, an outer peripheral surface of the cylindrical body at the open end may be subjected to round chamfering. With this configuration, in the gas sensor, the outer peripheral surface of the cylindrical body at the open end is subjected to the round chamfering. The present inventors have experimentally confirmed that a possibility of breakage of the tube can be suppressed by subjecting the outer peripheral surface of the cylindrical body at the open end to the round chamfering. When the outer peripheral surface of the cylindrical body at the open end is not subjected to the round chamfering, a corner of the outer peripheral surface of the cylindrical body at the open end comes into contact with the tube disposed between the gripping member and the cylindrical body, and a stress is concentrated at the contact position, so that the tube is easily broken. By subjecting the outer peripheral surface of the cylindrical body at the open end to the round chamfering, stress concentration is alleviated, so that the possibility of the breakage of the tube can be suppressed. Therefore, by subjecting the outer peripheral surface of the cylindrical body at the open end to the round chamfering, the gas sensor exerts an effect that the possibility of the breakage of the tube can be suppressed.

According to the present invention, it is possible to provide a gas sensor in which a possibility that a gripping position of a gripping member is moved by an external impact and a gripping force is reduced is suppressed.

BRIEF DESCRIPTION OF DRAWINGS

FIG. 1 is a schematic partially cross-sectional view schematically showing one example of a main configuration of a gas sensor according to an embodiment;

FIG. 3 is a view for describing an angle of an inclined portion of a caulked portion included in the gas sensor of FIG. 1;

FIG. 4A is views showing comparison between a case where an outer peripheral surface of a rear end of a cylindrical body included in the gas sensor is not subjected to round chamfering and a case where the outer peripheral surface is subjected to the round chamfering;

FIG. 4B is views showing comparison between a case where an outer peripheral surface of a rear end of a cylindrical body included in the gas sensor is not subjected to round chamfering and a case where the outer peripheral surface is subjected to the round chamfering.

DETAILED DESCRIPTION OF THE
PREFERRED EMBODIMENTS

Hereinafter, an embodiment (hereinafter, also referred to as "the present embodiment") according to one aspect of the present invention will be described with reference to the drawings. However, the present embodiment described below is merely an example of the present invention in all respects. It goes without saying that various improvements and modifications can be made without departing from the scope of the present invention. That is, in carrying out the present invention, a specific configuration according to the embodiment may be appropriately adopted.

Figure 5:
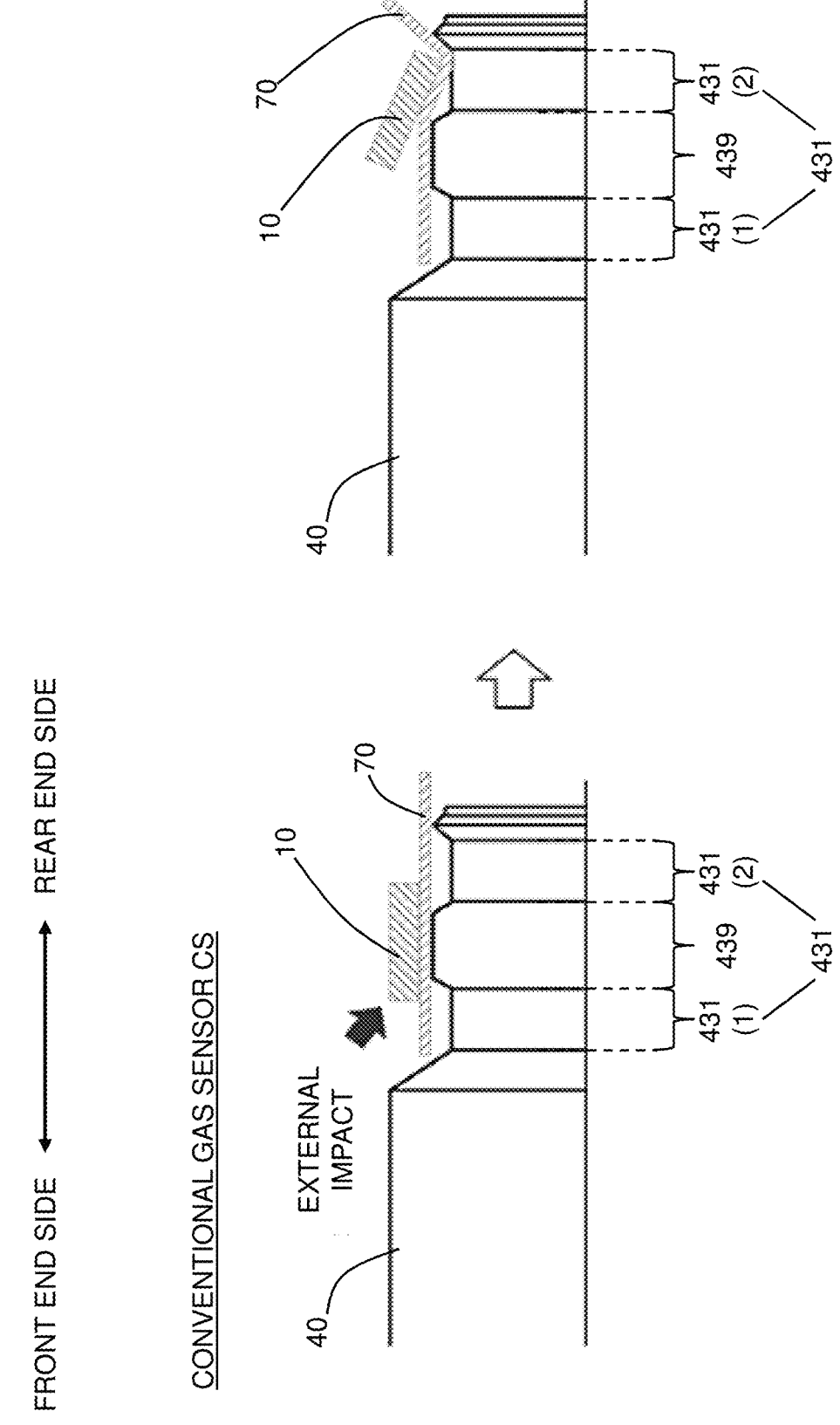
FIG. 5 is enlarged cross-sectional views each schematically showing a main part of a conventional gas sensor CS.

The present inventors have found a problem that, for a gas sensor such as the conventional gas sensor CS illustrated in FIG. 5, there is a possibility that the gripping member 10 is displaced due to an external impact, and the gripping force of the gripping member 10 may be reduced when the displacement occurs. For example, as illustrated in FIG. 5, in the conventional gas sensor CS, the caulked portions 431 each caulked in a radially reduced shape are formed on the rear end side of the cylindrical body 40. In the conventional gas sensor CS, the gripping member 10 may grip the outer peripheral surface covered with the tube 70 of the cylindrical body 40, that is, the outer peripheral surface of the crest portion 439 (that is, the portion where the caulked portion 431 is not formed). Therefore, when the gripping member 10 is displaced due to an external impact, in particular, when the position of the gripping member 10 (the gripping position) moves from the outer peripheral surface of the crest portion 439 to the outer peripheral surface of the caulked portion 431 as illustrated in FIG. 5, the gripping force of the gripping member 10 may be reduced. The present inventors have found that the above-described problem of "the gripping member 10 may be displaced, and the gripping force of the gripping member 10 may be reduced" may occur in the conventional gas sensor CS, and have studied a method for solving the problem.

The present inventors conducted an experiment, and confirmed that by disposing the gripping member in the caulked portion formed by caulking a part of the rear end side of the cylindrical body 40 in a radially reduced shape, the possibility that the gripping member is displaced due to an external impact can be suppressed. That is, it has been confirmed that the gripping member that grips the "outer peripheral surface covered with the tube of the caulked portion is less likely to cause displacement than the conventional gripping member that grips the "outer peripheral surface covered with the tube of the cylindrical body 40 where the caulked portion is not formed".

Therefore, in a gas sensor according to one aspect of the present invention, a gripping member grips an outer peripheral surface covered with a tube of a caulked portion, the caulked portion being formed by caulking a part of a rear end side of a cylindrical body 40 in a radially reduced shape. By adopting such a configuration, the gas sensor according to one aspect of the present invention has an effect that as compared with the conventional gas sensor CS, the possibility can be suppressed that the position of the gripping member (the gripping position) is moved by an external impact and the gripping force of the gripping member is reduced.

In particular, in the gas sensor according to the one aspect of the present invention, the caulked portion includes two inclined portions and a bottom portion. Each of the two inclined portions is a portion where a diameter of the cylindrical body 40 continuously changes along an axial direction of the cylindrical body 40. The bottom portion is a portion that is disposed between the above-described two inclined portions in the axial direction of the cylindrical body 40 and has a constant diameter of the cylindrical body 40 along the axial direction of the cylindrical body 40. The two inclined portions are each formed in, for example, a tapered shape or a rounded shape.

The present inventors conducted an experiment to identify a desirable range of an angle of each of the inclined portions of the caulked portion. As a result, it has been confirmed that when the inclined portion has a tapered shape, that is, when the inclined portion is formed so as to have a straight line in a cross section parallel to a longitudinal axis of the gas sensor (the cylindrical body 40) and in contact with the axis, the angle of the inclined portion is desirably within a range below. That is, the present inventors have confirmed that it is desirable to set an angle (hereinafter, also referred to as an "angle α") between the inclined portion and a plane obtained by extending the bottom portion toward a side of the inclined portion to 30° or more. In addition, since the inclined portion is a portion where the diameter of the cylindrical body 40 continuously changes along the axial direction of the cylindrical body 40, the angle α is less than 90°. Therefore, the present inventors have confirmed that it is desirable to set the angle α to 30° or more and less than 90°.

In addition, the present inventors have confirmed that, when the inclined portion has a rounded shape, that is, when the inclined portion is formed so as to have a curved line in the cross section parallel to the longitudinal axis of the gas sensor (the cylindrical body 40) and in contact with the axis, it is desirable to set the angle of the inclined portion within a range below. That is, the present inventors have confirmed that it is desirable to set an angle between a plane parallel to a tangent of the inclined portion at a contact point between the inclined portion and the bottom portion and a plane obtained by extending the bottom portion toward the side of the inclined portion (hereinafter, also referred to as an "angle β") to 30° or more. In addition, similarly to the angle α, the angle β is also less than 90°. Therefore, the present inventors have confirmed that it is desirable to set the above-described angle β to 30° or more and less than 90°.

The present inventors have experimentally confirmed that when the inclined portion has a tapered shaped, the gripping position of the gripping member can be reliably fixed by the inclined portion by setting the angle α to 30° or more and less than 90°. In addition, the present inventors have experimentally confirmed that when the inclined portion has a rounded shape, the gripping position of the gripping member can be reliably fixed by the inclined portion by setting the angle β to 30° or more and less than 90°. When each of the angle α and the angle β is set to less than 30°, the position of the gripping member (the gripping position) cannot be reliably fixed by the inclined portion, and the gripping position of the gripping member is easily moved (easily displaced) by an external impact, and the gripping force is reduced.

Therefore, the angle α of the inclined portion is set to 30° or more and less than 90°, or the angle β is set to 30° or more and less than 90°, whereby the gas sensor according to the one aspect of the present invention exerts the effect below. That is, the gas sensor according to the one aspect of the present invention exerts the effect of reliably fixing the gripping position of the gripping member by the inclined portion of the caulked portion. Hereinafter, a gas sensor 1 will be described as the gas sensor according to the one aspect of the present invention with reference to FIGS. 1 to 4.

Configuration Example

<Overall Outline of Gas Sensor>

Figure 1:
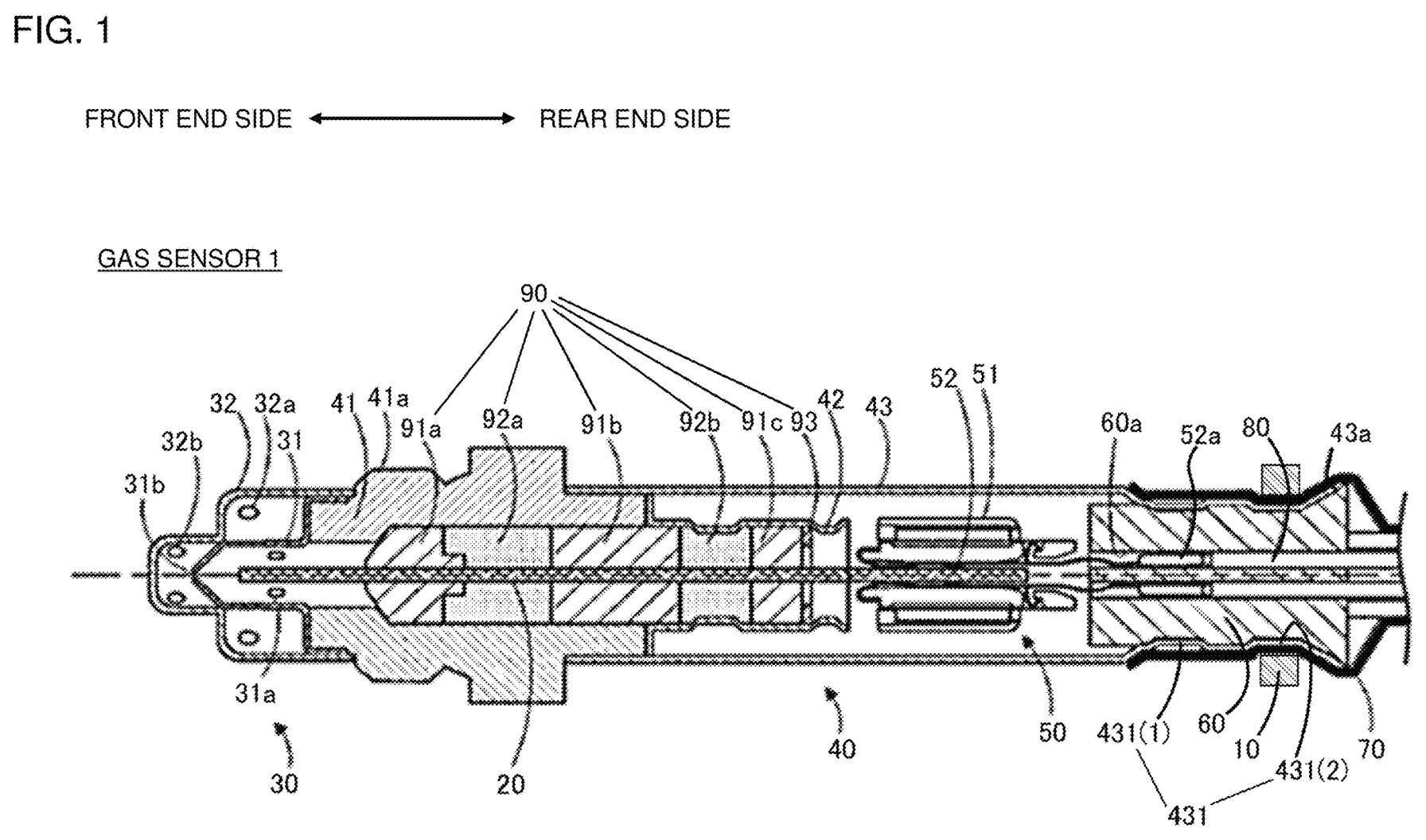

FIG. 1 is a schematic cross-sectional view schematically showing one example of a configuration of the gas sensor 1 according to the present embodiment. That is, FIG. 1 schematically shows a configuration of a cross section of the gas sensor 1 parallel to and in contact with a longitudinal axis (an axis line, a line along a right-left direction in the drawing). The gas sensor 1 is one example of a "gas sensor" of the present invention, and is a gas sensor capable of detecting a concentration (a specific gas concentration) of a specific gas such as oxygen or $NO_x$ in a gas to be measured such as an exhaust gas of an automobile. As illustrated in FIG. 1, the gas sensor 1 has an axis and is configured to extend along the longitudinal direction (the axial direction), and has a front end and a rear end as respective ends in the longitudinal direction. One end in the longitudinal direction is the front end, and another end is the rear end. In the example of FIG. 1, the gas sensor 1 is disposed such that the front end of the gas sensor 1 faces a left direction and a rear end of the gas sensor 1 faces a right direction. That is, the right-left direction in FIG. 1 corresponds to the longitudinal direction (axial direction). In the present embodiment, the gas sensor 1 includes a gripping member 10, a sensor element 20, a protective cover 30, a cylindrical body 40, a connector 50, an elastic body 60, a tube 70, lead wires 80, and an annular component 90. In the gas sensor 1, the sensor element 20 is surrounded by the cylindrical body 40 and the protective cover 30, and the cylindrical body 40 and the protective cover 30 configure a housing member (a casing) that houses the sensor element 20 thereinside as a whole. The sensor element 20 is disposed coaxially with the cylindrical body 40 and the protective cover 30, and an extending direction of a central axis of the sensor element 20 coincides with the axial direction of the gas sensor 1.

(Sensor Element)

The sensor element 20 is one example of a "sensor element" of the present invention, and is configured to extend along the axial direction (the right-left direction in FIG. 1). The sensor element 20 illustrated in FIG. 1 is an elongated flat plate-shaped (an elongated plate-shaped) element. The sensor element 20 has a detection unit (not shown) on a front end side and connector electrodes (not shown) on a rear end side. The front end side of the sensor element 20 may be coated with an outer porous layer, and the outer porous layer may serve as a protective layer that suppresses occurrence of a crack in an element body of the sensor element 20 due to adhesion of moisture or the like in the gas to be measured, for example.

In the gas sensor 1, the sensor element 20 is disposed such that the front end side faces the front end of the gas sensor 1. For example, in one aspect of the sensor element 20, the gas to be measured introduced into the sensor element 20 is reduced or decomposed inside the sensor element 20 to generate oxygen ions. In the gas sensor 1 including the above-described sensor element 20, the concentration of the specific gas is obtained on the basis of a fact that an amount of the oxygen ions flowing inside the sensor element 20 is proportional to the concentration of the specific gas that is a sensing target gas in the gas to be measured.

In the example shown in FIG. 1, the front end side of the sensor element 20 is surrounded by the protective cover 30, the rear end side protrudes into an outer cylinder 43, and a substantially central portion between the front end side and the rear end side is fixed to insides of a main metal fitting 41 and an inner cylinder 42 in such a manner that both end portions are airtightly sealed by the annular component 90.

(Annular Component)

In the example shown in FIG. 1, the annular component 90 includes a plurality of ceramic supporters 91a, 91b, 91c, a plurality of green compacts 92a, 92b, and a metal ring 93. Each of the ceramic supporters 91a, 91b, 91c is an insulator made of ceramics. More specifically, a through hole (not shown) having a shape corresponding to a cross-sectional shape of the sensor element 20 is provided at an axial center position of each of the ceramic supporters 91a, 91b, 91c, and the sensor element 20 is inserted into the through holes, whereby the ceramic supporters 91a, 91b, 91c are annularly mounted on the sensor element 20. Note that the ceramic supporter 91a is locked to a tapered surface of the main metal fitting 41 on a left side in the drawing.

On the other hand, each of the green compacts 92a, 92b is formed by molding a ceramic powder such as talc. Similarly to the ceramic supporters 91a, 91b, 91c, the green compacts 92a, 92b are formed by inserting the sensor element 20 into through holes and disposing two molded bodies (not shown) annularly mounted on the sensor element 20 inside the main metal fitting 41 and the inner cylinder 42 in a state of being annually mounted around the sensor element 20, and then further compressing and integrating the green compacts 92a, 92b. In the example shown in FIG. 1, the green compact 92a is filled between the ceramic supporters 91a, 91b, and the green compact 92b is filled between the ceramic supporters 91b, 91c. As illustrated in FIG. 1, the ceramic supporters 91a, 91b, 91c and the green compacts 92a, 92b are sealed inside the main metal fitting 41 and the inner cylinder 42, and these are sandwiched and sealed between the metal ring 93, an inner wall of the main metal fitting 41, and an inner wall of the inner cylinder 42. The compressed filling of the green compacts 92a, 92b achieves airtight sealing between the front end side and the rear end side of the sensor element 20.

FIG. 1 shows an example in which the annular component 90 is configured of the plurality of ceramic supporters 91a, 91b, 91c, the plurality of green compacts 92a, 92b, and the metal ring 93. However, in the gas sensor 1, it is not essential that the annular component 90 is configured of the ceramic supporters 91a, 91b, 91c, the green compacts 92a, 92b, and the metal ring 93. The gas sensor 1 illustrated in FIG. 1 includes the annular component 90 that fixes the sensor element 20 inside the main metal fitting 41 and the inner cylinder 42 and airtightly seals between the front end side and the rear end side of the sensor element 20.

(Cylindrical Body)

The cylindrical body 40 is one example of a "cylindrical body" of the present invention, and is a cylindrical member in which the sensor element 20 is disposed thereinside and an open end is formed. The cylindrical body 40 is made of, for example, metal, and in the example shown in FIG. 1, the sensor element 20 and the connector 50 are disposed inside the cylindrical body 40. The cylindrical body 40 may be configured by coaxially disposing a plurality of cylindrical members each of which is a metal member. In the example shown in FIG. 1, the cylindrical body 40 includes the cylindrical main metal fitting 41, the cylindrical inner cylinder 42, the cylindrical outer cylinder 43, and a fixing bolt 41a, each of which is a metal member.

Each of the main metal fitting 41 and the inner cylinder 42 is a cylindrical (for example, a round cylindrical shape)

member made of metal. The inner cylinder 42 is welded and fixed to the main metal fitting 41, and for example, is welded and fixed to a rear end side of the main metal fitting 41 in the axial direction. Inside the main metal fitting 41 and the inner cylinder 42, the sensor element 20 and the annular component 90 for fixing, which is annularly mounted on the sensor element 20, are housed. That is, the main metal fitting 41 and the inner cylinder 42 are further annularly mounted around the annular component 90 annularly mounted around the sensor element 20. The main metal fitting 41 and the inner cylinder 42 illustrated in FIG. 1 are configured to surround the sensor element 20 along the axial direction (the longitudinal direction), and are particularly configured to surround a range excluding a part of each of the front end side and the rear end side of the sensor element 20.

The outer cylinder 43 is a cylindrical (for example, a round cylindrical shape) member made of metal, and the outer cylinder 43 illustrated in FIG. 1 covers the rear end of the sensor element 20 and a periphery of the connector 50.

An end portion (an open end) on a front end side of the outer cylinder 43 is welded and fixed to an outer peripheral end portion on the rear end side of the main metal fitting 41. In addition, the elastic body 60 is disposed at an open end (the open end 43a) on a rear end side of the outer cylinder 43 so as to seal the open end. The caulked portions 431 for caulking a part of the elastic body 60 for sealing the open end on the rear end side from a periphery are formed on the rear end side of the outer cylinder 43.

In the example shown in FIG. 1, the two caulked portions 431 are formed on the rear end side of the outer cylinder 43, and specifically, a caulked portion 431(1) and a caulked portion 431(2) are formed. In the present embodiment, when it is not necessary to distinguish the caulked portion 431(1) and the caulked portion 431(2) from each other, they may be simply described as the "caulked portion(s) 431". In addition, when the plurality of caulked portions 431 are distinguished from each other, "(1)", "(2)", "(3)", . . . , "(n)", and "(n+1)" are added after the member number "431" to distinguish each of the plurality of caulked portions. "n" is an integer of "1" or more.

The caulked portion 431 is one example of a "caulked portion" of the present invention. In the caulked portion 431, the outer cylinder 43 is caulked from an outside in a radially reduced shape over an entire circumferential direction thereof, so that a reaction force directed radially outward is generated in the elastic body 60, whereby the outer cylinder 43 is sealed.

In addition, from the open end 43a on the rear end side of the outer cylinder 43 sealed by the elastic body 60, the lead wires 80 are each drawn out to the outside through a through hole 60a formed an inside of the elastic body 60. Outside air (atmosphere) is introduced into an internal space of the outer cylinder 43 through between a coating of each of the lead wires 80 and a metal wire (conductor) (in other words, an inside of the coating), and the internal space of the outer cylinder 43 becomes a reference gas (ambient air) atmosphere. The rear end of the sensor element 20 is disposed in the internal space of the outer cylinder 43 filled with the reference gas.

The fixing bolt 41a is an annular member used to fix the gas sensor 1 to a measurement position (an attachment position), and is fixed coaxially with the main metal fitting 41. The fixing bolt 41a includes a threaded bolt portion and a held portion held when the bolt portion is screwed. The bolt portion of the fixing bolt 41a is screwed with a nut provided at the attachment position of the gas sensor 1. For example, when the bolt portion of the fixing bolt 41a is screwed into a nut (a nut portion) provided in an exhaust pipe of an automobile, the gas sensor 1 is fixed to the exhaust pipe in a mode in which a side of the protective cover 30 is exposed to the exhaust pipe.

As described above, the cylindrical body 40 illustrated in FIG. 1 includes the main metal fitting 41, the inner cylinder 42, the outer cylinder 43, and the fixing bolt 41*a*, and is configured as a cylindrical member as a whole (for example, a round cylindrical shape), particularly as a cylindrical member extending in the axial direction. That is, the cylindrical body 40 illustrated in FIG. 1 is a round cylindrical member extending in the axial direction, including the cylindrical main metal fitting 41, the round cylindrical inner cylinder 42 and outer cylinder 43 welded and fixed to the main metal fitting 41, and the fixing bolt 41*a* disposed on an outer periphery on a front end side of the main metal fitting 41. For example, the cylindrical body 40 and the gas sensor 1 (the sensor element 20) are coaxial, and the cylindrical body 40 has a front end and a rear end as ends in the axial direction (longitudinal direction), and is disposed such that the front end of the cylindrical body 40 faces the front end of the gas sensor 1. The cylindrical body 40 houses the sensor element 20, the annular component 90 for fixing annularly mounted on the sensor element 20, and the connector 50, and the open end 43*a* on a rear end side is sealed by the elastic body 60. The caulked portions 431 for fixing the elastic body 60 for sealing the open end 43*a* of the cylindrical body 40 are formed on the rear end side of the cylindrical body 40 (the outer cylinder 43), and the caulked portions 431 caulk a part of the elastic body 60 from the periphery.

Note that in the gas sensor 1, it is not essential that the cylindrical body 40 includes the main metal fitting 41, the inner cylinder 42, the outer cylinder 43, and the fixing bolt 41*a*. The cylindrical body 40 may not include the fixing bolt 41*a*, and the main metal fitting 41, the inner cylinder 42, and the outer cylinder 43 may be members integrally formed. In the gas sensor 1, the cylindrical body 40 may be a cylindrical member in which the sensor element 20 is disposed thereinside and an open end is formed.

(Connector)

The connector 50 includes a housing 51 made of ceramics such as an alumina sintered body, and contact fittings 52 held by the housing 51 and in contact with the electrodes (for example, the connector electrodes) of the sensor element 20. The contact fittings 52 are drawn out to an outside of the connector 50 and are electrically connected to the lead wires 80 at connection portions 52*a* that are crimp terminals. Note that the connector 50 includes the contact fittings 52 of a number (for example, four, eight, or the like) corresponding to a number of electrodes formed on a front surface and a back surface of the sensor element 20. Therefore, the connection portions 52*a* are provided at a plurality of locations (for example, four locations, eight locations, and the like), and the plurality of (for example, four, eight, or the like) lead wires 80 are also drawn out.

(Lead Wire)

Each of the lead wires 80 is one example of a "lead wire" of the present invention, is electrically connected to the sensor element 20, and extends outward from an inside of the cylindrical body 40 through the open end 43*a* of the cylindrical body 40. In the example shown in FIG. 1, the lead wire 80 is electrically connected to the connector electrode of the sensor element 20 via the contact fitting 52, and extends outward from the open end 43*a* of the cylindrical body 40. Specifically, the lead wire 80 is electrically connected to a rear end side (that is, the connection portion

52*a*) of the contact fitting 52 on a front end side thereof, and a rear end side of the lead wire 80 extends outward from the open end 43*a* of the cylindrical body 40. A gap between the lead wire 80 and the cylindrical body 40 (the outer cylinder 43) is sealed by the elastic body 60.

For example, the lead wire 80 is inserted into the through hole 60*a* provided inside elastic body 60. An end portion on the front end side of the lead wire 80 is crimped and fixed to the rear end side (the connection portion 52*a*) of the contact fitting 52, and an end portion on the rear end side of the lead wire 80 is connected to an external device (a controller), a power supply, or the like. As a result, the sensor element 20 (in particular, the connector electrode of the sensor element 20) is electrically connected to the external device, the power supply, and the like through the contact fitting 52 and the lead wire 80. Note that FIG. 1 shows an example in which there are two contact fittings 52 and two lead wires 80, but this is merely for simplicity of illustration. In practice, the gas sensor 1 includes the contact fittings 52 and the lead wires 80 as many as necessary for the above-described electrical connection.

In the gas sensor 1, for example, outside air and a gas inside the cylindrical body 40 pass between the coating of the lead wire 80 and the metal wire (a conductor) (in other words, the inside of the coating), whereby the outside air is introduced into the cylindrical body 40 and the gas inside the cylindrical body 40 is discharged to the outside.

(Elastic Body)

The elastic body 60 is a member having elasticity, and is made of, for example, rubber. The elastic body 60 is disposed so as to seal the open end 43*a* (the open end on the rear end side) of the cylindrical body 40, and the lead wires 80 are inserted thereinto. Specifically, the through holes 60*a* extending in the axial direction are formed inside the elastic body 60, and for example, the plurality of through holes 60*a* extending in the axial direction are formed. The lead wires 80 are housed (inserted) in the through holes 60*a* formed inside the elastic body 60, and for example, each of the plurality of lead wires 80 is housed (inserted) in each of the plurality of through holes 60*a* formed inside the elastic body 60.

A material of the elastic body 60 is, for example, fluororubber. Fluororubber has excellent properties in various aspects such as resistance and strength, and is particularly excellent in heat resistance and oil resistance. Therefore, the gas sensor 1 uses the elastic body 60 made of fluororubber, so that an effect is exerted that a sealing property of the elastic body 60 can be secured even in a high-temperature environment, for example, and a detection accuracy of the gas concentration can be maintained and improved. However, it is not essential for the gas sensor 1 to use fluororubber as the material of the elastic body 60, and the gas sensor 1 may appropriately use a material having elasticity as the material of the elastic body 60.

(Protective Cover)

The protective cover 30 is a substantially round cylindrical exterior member that protects a predetermined range on the front end side, which is a portion of the sensor element 20 that directly contacts the gas to be measured during use. The protective cover 30 illustrated in FIG. 1 is configured to surround a periphery of at least a part of the front end side of the cylindrical body 40 (the main metal fitting 41) along the axial direction (the longitudinal direction) and extend beyond the front end of the sensor element 20. For example, the protective cover 30 is configured to surround a part of the front end side of the sensor element 20 and the cylindrical body 40 around the axis. The protective cover 30 has a front end and a rear end as respective ends in the axial direction, and the front end of the protective cover 30 is disposed on the front end side of the gas sensor 1 with respect to the front end of the sensor element 20.

The protective cover 30 is provided with a plurality of through holes 31a, 31b, 32a, 32b through which the gas can pass. The gas to be measured that flows into the protective cover 30 through the through holes is a direct detection target in the sensor element 20. Note that types, a number of through holes, disposition positions, shapes, and the like of the through-holes provided in the protective cover 30 may be appropriately determined in consideration of an inflow mode of the gas to be measured into the protective cover 30.

In the example shown in FIG. 1, the protective cover 30 includes a bottomed cylindrical inner cover 31 that covers the front end of the sensor element 20 and a bottomed cylindrical outer cover 32 that covers the inner cover 31. The inner cover 31 is configured to cover at least a part of the peripheries of the sensor element 20 and the cylindrical body 40 (the main metal fitting 41) on the front end side, and includes the through holes 31a, 31b for circulating the gas to be measured. The outer cover 32 is configured to cover a periphery of the inner cover 31, and is formed in a bottomed cylindrical shape in the example shown in FIG. 1, and includes, in side surfaces, the through holes 32a, 32b for allowing the gas to be measured to flow.

A sensor element chamber is formed as a space surrounded by the inner cover 31, and the front end of the sensor element 20 is disposed inside this sensor element chamber. The sensor element chamber is connected to a space outside the protective cover 30 by the through holes 31a, 31b, 32a, 32b provided in the protective cover 30. However, a configuration and a shape of the protective cover 30 are not limited to such an example. The configuration and the shape of the protective cover 30 may be appropriately determined according to the embodiment.

As a material of the protective cover 30, for example, a metal material such as stainless steel (for example, SUS) may be used. The protective cover 30 may be manufactured by appropriately molding a metal material. The protective cover 30 may be omitted from the configuration of the gas sensor 1.

(Tube)

The tube 70 is one example of a "tube" of the present invention, and covers an outer peripheral surface of an end portion of the cylindrical body 40 including the open end 43a and portions of the lead wires 80 extending outward from the open end 43a of the cylindrical body 40. The tube 70 is an insulating and flexible cylindrical member, and covers the portions of the lead wires 80 extending outward from the open end 43a of the cylindrical body 40. In addition, the tube 70 covers an outer peripheral surface of an end portion on a base end side (rear end side) of the cylindrical body 40 (the outer cylinder 43) including the open end 43a and the caulked portions 431 (the caulked portions 431(1), 431(2)). In the present embodiment, the tube 70 is a varnish tube in which a silicone material is applied to a surface of a braided tube made of glass fibers. Note that a material of the tube 70 is not limited thereto, and may be, for example, resin fibers of polyester or the like instead of glass fibers. Note that the lead wires 80 are doubly covered with the covering of the lead wires 80 themselves and the tube 70.

(Gripping Member)

The gripping member 10 is one example of a "gripping member" of the present invention, and grips a portion covered with the tube 70 in an outer peripheral surface of the cylindrical body 40 such that the tube 70 protrudes to the side opposite to the open end 43a of the cylindrical body 40 in the axial direction. That is, the portion covered with the tube 70 of the outer peripheral surface of the cylindrical body 40 (the outer cylinder 43) is gripped by the gripping member 10. The gripping member 10 may be, for example, a metal ear clamp, and may include a ring portion and an ear portion (not shown). The ring portion and the ear portion may be formed by bending one plate-shaped member, and the ring portion may surround the outer peripheral surfaces of the tube 70 and the cylindrical body 40. In the gripping member 10, an inner peripheral surface of the ring portion may be in contact with the tube 70. An end portion of an arc of the ring portion may be accommodated in a groove formed in the inner peripheral surface of the ring portion. As a result, the gripping member 10 may be configured as a so-called stepless clamp having no step on the inner peripheral surface of the ring portion.

As described above, the gripping member 10 grips the portion covered with the tube 70 of the outer peripheral surface of the cylindrical body 40, that is, grips the cylindrical body 40 and the tube 70. The gripping member 10 is not limited to a clamp as long as it is a gripping member that grips the cylindrical body 40 and the tube 70, and any member may be used. For example, instead of the clamp, a resin binding band or the like may be used as the gripping member 10 to grip the cylindrical body 40 and the tube 70. In addition, the clamp and the binding band are ring-shaped members surrounding the outer peripheral surface of the cylindrical body 40, but the present invention is not limited thereto, and the gripping member 10 may be a member having a shape other than the ring shape, such as, for example, a C shape or a V shape.

In the gas sensor 1, unlike the gripping member 10 of the conventional gas sensor CS, the gripping member 10 grips the outer peripheral surface covered with the tube 70 of the caulked portion 431 formed on the rear end side of the cylindrical body 40. In particular, the gripping member 10 of the gas sensor 1 grips the outer peripheral surface covered with the tube 70 of the caulked portion 431 closest to the open end 43a of the cylindrical body 40 in the axial direction of the cylindrical body 40 among the one or more caulked portions 431 formed on the rear end side of the cylindrical body 40. In the example shown in FIG. 1, the gripping member 10 grips the outer peripheral surface covered with the tube 70 of the caulked portion 431(2) close to the open end 43a of the cylindrical body 40 among the caulked portion 431(1) on the front end side and the caulked portion 431(2) on the rear end side in the axial direction.

As described above with reference to FIG. 1, the gas sensor 1 includes the sensor element 20, the cylindrical body 40, the lead wires 80, the tube 70, and the gripping member 10. The cylindrical body 40 is a cylindrical member in which the sensor element 20 is disposed thereinside and the open end 43a is formed. The lead wires 80 are electrically connected to the sensor element 20 and extend outward from the inside of the cylindrical body 40 through the open end 43a of the cylindrical body 40. The tube 70 covers the outer peripheral surface of the end portion of the cylindrical body 40 including the open end 43a and the portions of the lead wires 80 extending outward from the open end 43a of the cylindrical body 40. The gripping member 10 grips the portion of the outer peripheral surface of the cylindrical body 40, the portion being covered with the tube 70 so that the tube 70 protrudes to the side opposite to the open end 43a of the cylindrical body 40. In the gas sensor 1, the one or more caulked portions 431 are formed on the side (rear end side) where the open end 43*a* of the cylindrical body 40 is formed, and in the example shown in FIG. 1, the caulked portion 431(1) and the caulked portion 431(2) are formed. The gripping member 10 grips the outer peripheral surface covered with the tube 70 of the caulked portion 431 closest to the open end 43*a* of the cylindrical body 40 in the axial direction of the cylindrical body 40 among the one or more caulked portions 431. In the example illustrated in FIG. 1, the gripping member 10 grips the outer peripheral surface covered with the tube 70 of the caulked portion 431(2) close to the open end 43*a* of the cylindrical body 40 among the caulked portion 431(1) and the caulked portion 431(2).

<Details of Rear End Side of Gas Sensor>

Figure 2:
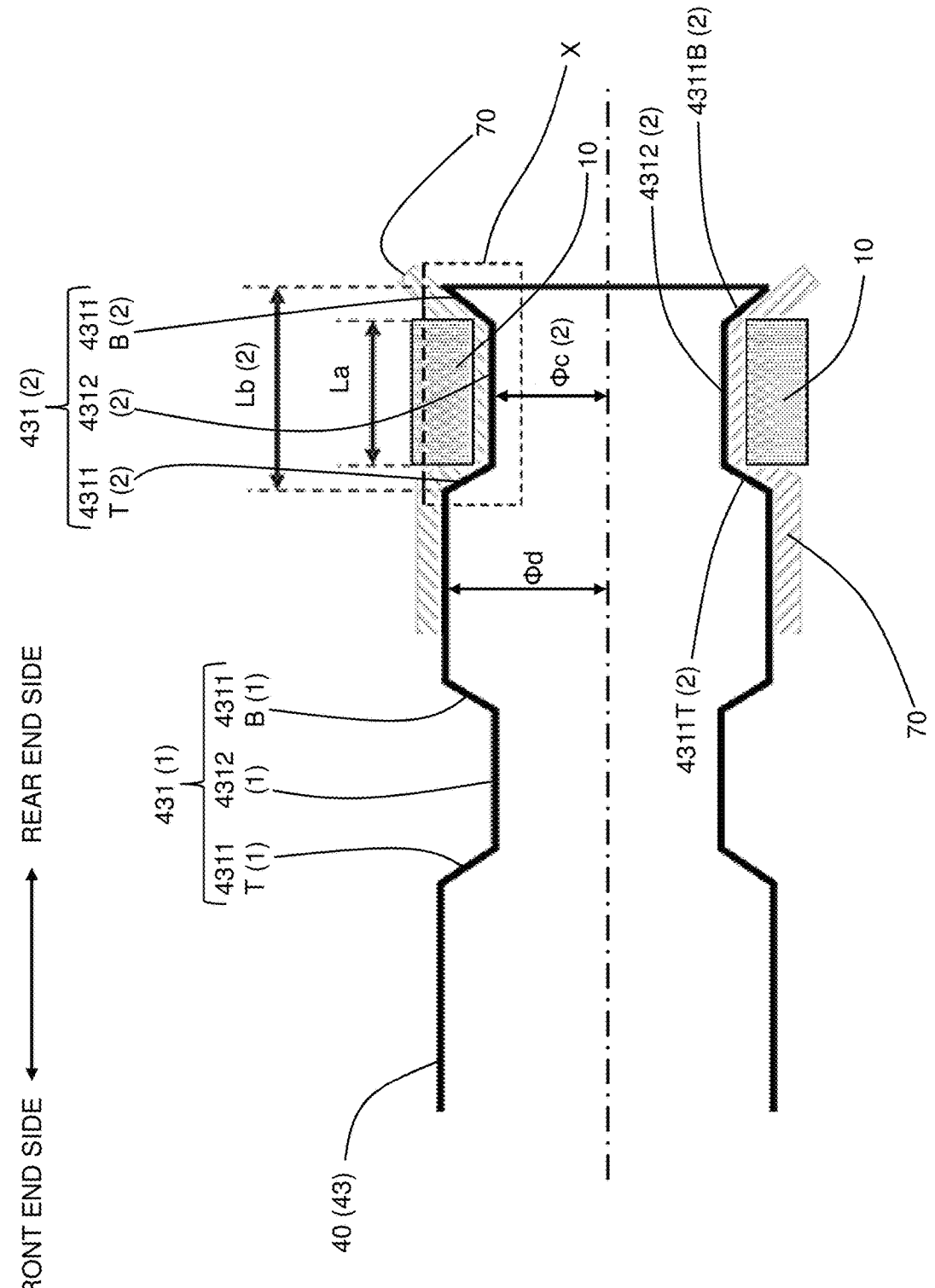
FIG. 2 is an enlarged cross-sectional view schematically showing a main part of the gas sensor of FIG. 1.

FIG. 2 is an enlarged cross-sectional view schematically showing a main part of the gas sensor 1. Specifically, FIG. 2 shows details of the rear end side of the gas sensor 1 (the side of the open end 43*a* of the cylindrical body 40). In FIG. 2, a right-left direction in the drawing is the axial direction (the longitudinal direction) of the gas sensor 1 (the sensor element 20), and a left side in the drawing is the front end side and a right side in the drawing is the rear end side.

(Configuration of Caulked Portion)

In the gas sensor 1, the one or more caulked portions 431 are formed on the rear end side (the side of the open end 43*a*) of the cylindrical body 40 (the outer cylinder 43) by caulking the cylindrical body 40 in a radially reduced shape over the entire circumferential direction. In the example shown in FIG. 2, the two caulked portions 431 are formed on the rear end side of the cylindrical body 40, and specifically, the caulked portion 431(1) and the caulked portion 431(2) are formed. The caulked portion 431(1) is formed on the front end side of the caulked portion 431(2) in the axial direction, that is, of the caulked portion 431(1) and the caulked portion 431(2), the caulked portion 431(2) is closer to the open end 43*a* (open end on the rear end side) of the cylindrical body 40.

The caulked portion 431 includes two inclined portions 4311 (an inclined portion 4311T on the front end side and an inclined portion 4311B on the rear end side in the axial direction), and a bottom portion 4312. In the example shown in FIG. 2, the caulked portion 431(1) includes an inclined portion 4311T(1), an inclined portion 4311B(1), and a bottom portion 4312(1). The caulked portion 431(2) includes an inclined portion 4311T(2), an inclined portion 4311B(2), and a bottom portion 4312(2).

In the following description, when it is not necessary to distinguish each of the inclined portion 4311T(1), the inclined portion 4311B(1), the inclined portion 4311T(2), and the inclined portion 4311B(2), they may be simply described as an "inclined portion(s) 4311". In particular, when it is not necessary to distinguish the inclined portion 4311T(1) and the inclined portion 4311B(1) of the caulked portion 431(1) from each other, they may be simply described as an "inclined portion(s) 4311(1)". Similarly, when it is not necessary to distinguish the inclined portion 4311T(2) and the inclined portion 4311B(2) of the caulked portion 431(2) from each other, they may be simply described as an "inclined portion 4311(2)". In addition, when it is not necessary to distinguish the bottom portion 4312(1) and the bottom portion 4312(2) from each other, they may be simply described as a "bottom portion(s) 4312".

In the inclined portion 4311, the diameter of the cylindrical body 40 continuously changes along the axial direction, and for example, the inclined portion 4311 is formed in a tapered shape or in a rounded shape. Specifically, the inclined portion 4311 may be formed so as to have a tapered shape, that is, a straight line (linear) in a cross section parallel to and in contact with the longitudinal axis of the gas sensor (cylindrical body 40). In addition, the inclined portion 4311 may be formed so as to have a rounded shape, that is, a curved line (curved shape) in a cross section parallel to and in contact with the longitudinal axis of the gas sensor (cylindrical body 40). In the example shown in FIG. 2, the inclined portion 4311T(1), the inclined portion 4311B(1), the inclined portion 4311T(2), and the inclined portion 4311B(2) are each formed in a tapered shape.

However, it is not essential for the gas sensor 1 to form each of the inclined portion 4311T(1), the inclined portion 4311B(1), the inclined portion 4311T(2), and the inclined portion 4311B(2) in a tapered shape. Each of the two inclined portions 4311 (that is, the inclined portion 4311T on the front end side and the inclined portion 4311B on the rear end side in the axial direction) of the caulked portion 431 may be formed in a tapered shape or in a rounded shape. One of the two inclined portions 4311 of the caulked portion 431 may be formed in a tapered shape and the other may be formed in a rounded shape. The two inclined portions 4311 of the caulked portion 431 may both be formed in a tapered shape, or the two inclined portions 4311 of the caulked portion 431 may both be formed in a rounded shape.

As described above, the diameter of the cylindrical body 40 continuously changes along the axial direction in the inclined portion 4311. Specifically, in the inclined portion 4311T on the front end side in the axial direction, the diameter of the cylindrical body 40 continuously changes along the axial direction such that the diameter on the front end side is larger than that on the rear end side. In addition, in the inclined portion 4311B on the rear end side in the axial direction, the diameter of the cylindrical body 40 continuously changes along the axial direction such that the diameter on the rear end side is larger than that on the front end side.

The bottom portion 4312 is disposed between the two inclined portions 4311 in the axial direction, that is, disposed between the inclined portion 4311T on the front end side and the inclined portion 4311B on the rear end side. In the example shown in FIG. 2, the bottom portion 4312(1) of the caulked portion 431(1) is disposed between the inclined portion 4311T(1) and the inclined portion 4311B(1) in the axial direction. In addition, the bottom portion 4312(2) of the caulked portion 431(2) is disposed between the inclined portion 4311T(2) and the inclined portion 4311B(2) in the axial direction.

In the bottom portion 4312, the diameter of the cylindrical body 40 is constant along the axial direction. In the example shown in FIG. 2, in the bottom portion 4312(1) of the caulked portion 431(1), the diameter of the cylindrical body 40 is constant along the axial direction. In addition, in the bottom portion 4312(2) of the caulked portion 431(2), the diameter of the cylindrical body 40 is constant along the axial direction.

(Position of Gripping Member)

In the gas sensor 1, the gripping member 10 grips the outer peripheral surface covered with the tube 70 of the caulked portion 431 closest to the open end 43*a* of the cylindrical body 40 in the axial direction among the one or more caulked portions 431 formed on the rear end side (the side of the open end 43*a*) of the cylindrical body 40. In the example shown in FIG. 2, the caulked portion 431(1) and the caulked portion 431(2) are formed on the rear end side of the cylindrical body 40, and of the caulked portion 431(1) and the caulked portion 431(2), the caulked portion 431(2) is closer to the open end 43*a* (the open end on the rear end side) of the cylindrical body 40. Therefore, in FIG. 2, the gripping member 10 grips the outer peripheral surface covered with the tube 70 of the caulked portion 431(2). In the example shown in FIG. 2, the gripping member 10 grips a region X, that is, grips the caulked portion 431(2), and the tube 70 covering the outer peripheral surface of the caulked portion 431(2). As described above, the two inclined portions 4311 (2) (the inclined portion 4311T(2) on the front end side and the inclined portion 4311B(2) on the rear end side) of the caulked portion 431(2) gripped by the gripping member 10 may each have a tapered shape or a rounded shape. One of the two inclined portions 4311(2) may have a tapered shape, and the other may have a rounded shape. The two inclined portions 4311(2) may both have a tapered shape, or the two inclined portions 4311(2) may both have a rounded shape.

The gripping member 10 grips the caulked portion 431 closest to the open end 43a of the cylindrical body 40 in the axial direction among the one or more caulked portions 431 formed on the rear end side of the cylindrical body 40, thereby achieving an effect below. That is, by forming the outer peripheral surface of the open end 43a of the cylindrical body 40 in a rounded shape, the gas sensor 1 can suppress "a possibility that the tube 70 comes into contact with a corner of the outer peripheral surface of the cylindrical body 40, and a stress concentrates on the corner (the contact position), so that the tube 70 is easily broken" by forming an outer peripheral surface of the open end 43a (the rear end) of the cylindrical body 40 in a rounded shape, for example. In order to achieve such an effect of preventing the breakage of the tube 70, as a premise, it is desirable that the gripping member 10 grips the tube 70 and the cylindrical body 40 at the caulked portion 431 on the most rear end side among the one or more caulked portions 431. When the gripping member 10 grips the caulked portion 431 closest to the open end 43a of the cylindrical body 40 in the axial direction among the one or more caulked portions 431, and the outer peripheral surface of the open end 43a of the cylindrical body 40 has a rounded shape, the gas sensor 1 can effectively prevent breakage of the tube 70. However, it is not essential for the gas sensor 1 to form the outer peripheral surface of the open end 43a of the cylindrical body 40 in a rounded shape in order to prevent the breakage of the tube 70. Details of an example in which the outer peripheral surface of the open end 43a is formed in a rounded shape will be described later.

(Axial Length of Gripping Member)

In the gas sensor 1, an axial length La of the gripping member 10 may be equal to or less than an axial length Lb(2) of the caulked portion 431(2) gripped by the gripping member 10. In the example shown in FIG. 2, the axial length La of the gripping member 10 is equal to or less than the axial length Lb(2) of the caulked portion 431(2). In particular, in the example shown in FIG. 2, the axial length La of the gripping member 10 is substantially equal to an axial length of the bottom portion 4312(2) of the caulked portion 431(2) and slightly longer than the axial length of the bottom portion 4312(2). However, the axial length La of the gripping member 10 may be equal to or less than the axial length of the bottom portion 4312(2) of the caulked portion 431(2). For example, a front end position of the gripping member 10 in the axial direction may be on the rear end side in the axial direction with respect to a front end position of the bottom portion 4312(2) in the axial direction. Similarly, a rear end position of the gripping member 10 in the axial direction may be on the front end side in the axial direction with respect to a rear end position of the bottom portion 4312(2) in the axial direction.

In the example shown in FIG. 2, a center position of the gripping member 10 in the axial direction coincides with (substantially coincides with) a center position of the caulked portion 431(2) in the axial direction (for example, a center position of the bottom portion 4312(2)). As illustrated in FIG. 2, the gripping member 10 may grip the outer peripheral surface of each of the inclined portion 4311T(2), the bottom portion 4312(2), and the inclined portion 4311B (2) of the caulked portion 431(2) covered with the tube 70. For example, the front end position of the gripping member 10 in the axial direction may be on the rear end side in the axial direction with respect to a front end position of the inclined portion 4311T(2) in the axial direction. Similarly, the rear end position of the gripping member 10 in the axial direction may be on the front end side in the axial direction with respect to a rear end position of the inclined portion 4311B(2) in the axial direction.

As described above, in the gas sensor 1, the axial length La of the gripping member 10 (the axial direction of the cylindrical body 40) may be equal to or less than the axial length Lb of the caulked portion 431(2) gripped by the gripping member 10. The present inventors have studied a relationship that the axial length of the gripping member 10 and the axial length Lb of the caulked portion 431(2) gripped by the gripping member 10 should be satisfied. The present inventors have experimentally confirmed that the gripping force of the gripping member 10 can be improved by setting the axial length La of the gripping member 10 to be equal to or less than the axial length Lb of the caulked portion 431(2). Therefore, by setting the axial length La of the gripping member 10 to be equal to or less than the axial length Lb of the caulked portion 431(2), the gas sensor 1 exerts an effect that a gripping force of the gripping member 10 can be improved.

(Diameter of Cylindrical Body in Caulked Portion)

In the gas sensor 1, a diameter Φd of a portion of the cylindrical body 40 where the caulked portion 431 is not formed may be larger by 0.5 mm or more than a diameter Φc(2) of the cylindrical body 40 at the bottom portion 4312(2) of the caulked portion 431(2) gripped by the gripping member 10. In the example shown in FIG. 2, the diameter Φd of the portion of the cylindrical body 40 where the caulked portion 431 is not formed is larger by 0.5 mm or more than the diameter Φc(2) of the cylindrical body 40 at the bottom portion 4312(2) of the caulked portion 431(2).

As described above, in the gas sensor 1, the diameter Φd of the portion of the cylindrical body 40 where the caulked portion 431 is not formed may be larger than the diameter Φc(2) of the cylindrical body 40 at the bottom portion 4312(2) of the caulked portion 431(2) gripped by the gripping member 10 by 0.5 mm or more.

When a difference in the diameter of the cylindrical body 40 is small between the portion where the caulked portion 431 is not formed and the bottom portion 4312(2) of the caulked portion 431(2), for example, when the bottom portion 4312(2) of the caulked portion 431(2) is not sufficiently deeper than the portion where the caulked portion 431 is not formed, a problem below may occur. That is, the gripping position of the gripping member 10 cannot be reliably fixed by the caulked portion 431(2), the gripping position of the gripping member 10 is easily moved by an external impact, and the gripping force of the gripping member 10 may be reduced. By making the bottom portion 4312(2) of the caulked portion 431(2) sufficiently deeper than the portion where the caulked portion 431 is not formed, the gripping position of the gripping member 10 can be reliably fixed by the caulked portion 431(2), and the movement of the gripping position and the reduction in the gripping force can be prevented. Specifically, by making the bottom portion 4312(2) of the caulked portion 431(2) sufficiently deeper by 0.5 mm or more than the portion where the caulked portion 431 is not formed, the gripping position of the gripping member 10 can be reliably fixed by the caulked portion 431(2), and the movement of the gripping position and the reduction in the gripping force can be prevented.

Therefore, the diameter of the portion of the cylindrical body 40 where the caulked portion 431 is not formed is made larger by 0.5 mm or more than the diameter of the cylindrical body 40 in the bottom portion 4312(2) of the caulked portion 431(2), by which the gas sensor 1 exerts an effect below. That is, the gas sensor 1 exerts an effect that the gripping position of the gripping member 10 can be reliably fixed by the caulked portion 431(2), and the movement of the gripping position and the reduction in the gripping force of the gripping member 10 can be prevented.

As shown in FIG. 2, the gripping member 10 is positioned so as to straddle the outer peripheral surface of the caulked portion 431(2) on the rear end side of the caulked portion 431(1) on the front end side and the caulked portion 431(2) on the rear end side. In addition, the tube 70 exists up to the front end side (the left direction in FIG. 2) with respect to the gripping member 10. That is, the tube 70 protrudes from the gripping member 10 to the side opposite to the open end 43*a*. A protrusion amount of the tube 70 is not particularly limited as long as a value exceeds 0 mm, and is, for example, 0.5 to 1.0 mm. In addition, an outer diameter of the open end 43*a* of the cylindrical body 40 is larger than an inner diameter of the gripping member 10. That is, the open end 43*a* of the cylindrical body 40 is a large-diameter portion having an outer diameter larger than the inner diameter of the gripping member 10. Note that a maximum diameter of the elastic body 60 (a maximum value of the diameter of a portion of the elastic body 60 not caulked by the caulked portion 431) and a maximum diameter of the tube 70 (a maximum diameter of a portion of the tube 70 not gripped by the gripping member 10) are both larger than the inner diameter of the gripping member 10. For example, the outer diameter of the open end 43*a* of the cylindrical body 40 is larger than the inner diameter of the gripping member 10, the maximum diameter of the elastic body 60 is larger than the outer diameter of the open end 43*a* of the cylindrical body 40, and the maximum diameter of the tube 70 is larger than the maximum diameter of the elastic body 60. Note that the maximum diameter of the elastic body 60 can also be regarded as an outer diameter of a portion having a largest diameter in a portion of the elastic body 60 closer to the open end 43*a* with respect to the gripping member 10, and can also be regarded as a diameter (an outer diameter) of a portion of the elastic body 60 protruding outward from the open end 43*a*. Similarly, the maximum diameter of the tube 70 can also be regarded as a diameter (an outer diameter) of a portion of the tube 70 covering the outer periphery of the portion of the elastic body 60 protruding outward from the open end 43*a*. For example, the maximum diameter of the tube 70 may be a value obtained by adding twice a thickness of the tube 70 to the maximum diameter of the elastic body 60.

(Angle of Inclined Portion in Caulked Portion)

Figure 3:
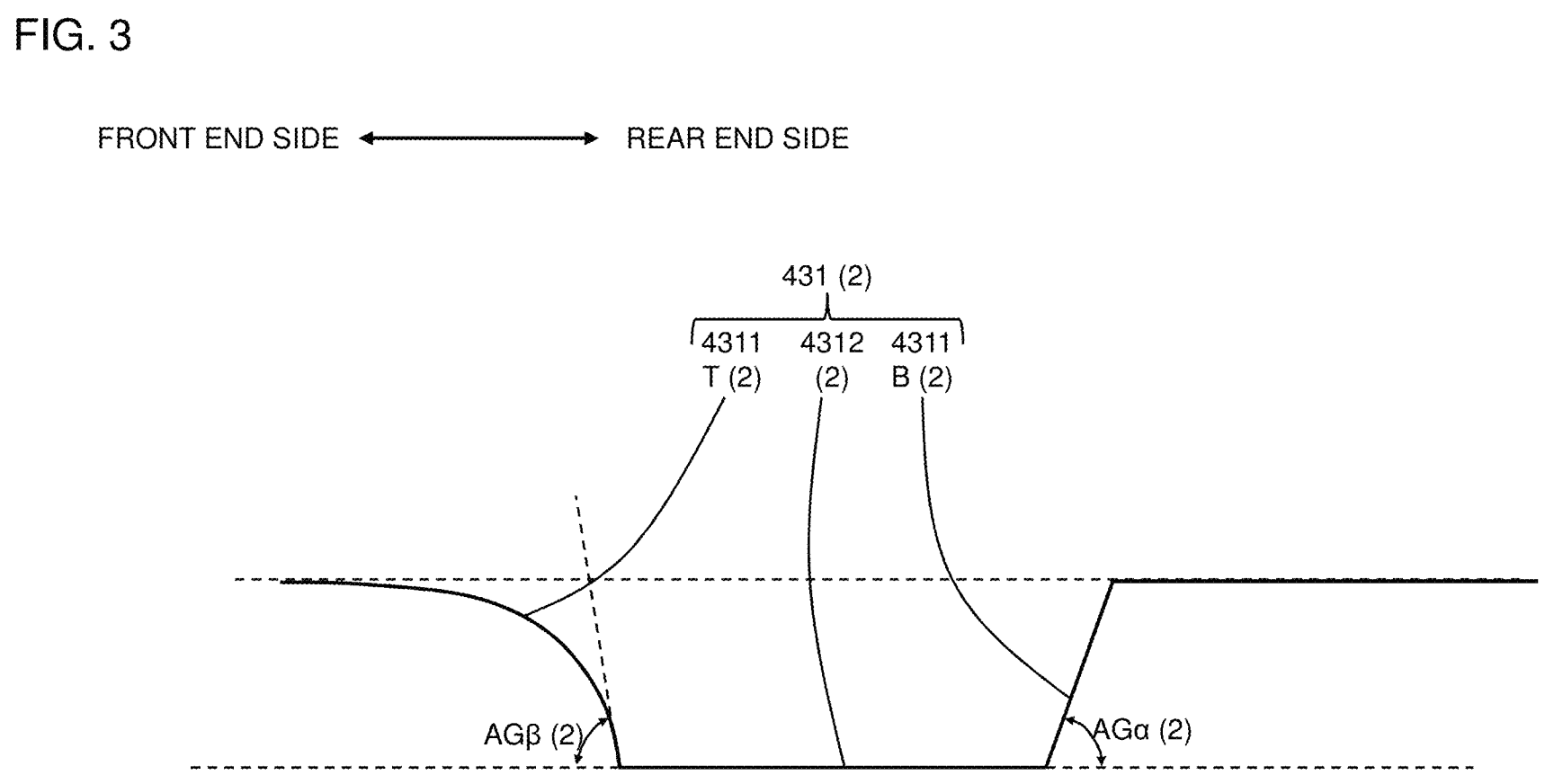

FIG. 3 is a view for describing an angle AG of each of the inclined portions 4311(2) (that is, the inclined portion 4311T(2) on the front end side and the inclined portion 4311B(2) on the rear end side in the axial direction) of the caulked portion 431(2) gripped by the gripping member 10. Specifically, FIG. 3 schematically shows a configuration of the cross section of the caulked portion 431(2) parallel to and in contact with the longitudinal axis (the axis line, a line along the left-right direction in the drawing) of the gas sensor 1 (the cylindrical body 40). In the example of FIG. 3, a left direction in the drawing is the front end side of the gas sensor 1, and a right direction in the drawing is the rear end side of the gas sensor 1.

As described above, the two inclined portions 4311(2) (the inclined portion 4311T(2) on the front end side and the inclined portion 4311B(2) on the rear end side) of the caulked portion 431(2) may each have a tapered shape or a rounded shape. In the example shown in FIG. 3, the inclined portion 4311T(2) on the front end side is formed so as to have a rounded shape, that is, a curved line (curved shape) in the cross section parallel to and in contact with the longitudinal axis of the gas sensor. That is, in the inclined portion 4311T(2) on the front end side, the diameter of the cylindrical body 40 continuously changes along the axial direction such that the diameter on the front end side is larger than that on the rear end side, and the inclined portion 4311T(2) on the front end side is drawn as a curved line in the cross section shown in FIG. 3. In addition, the inclined portion 4311B (2) on the rear end side is formed so as to have a tapered shape, that is, a straight line (linear) in the cross section parallel to and in contact with the longitudinal axis of the gas sensor. That is, in the inclined portion 4311B(2) on the rear end side, the diameter of the cylindrical body 40 continuously changes along the axial direction such that the diameter on the rear end side is larger than that on the front end side, and the inclined portion 4311B(2) on the rear end side is drawn as a straight line in the cross section shown in FIG. 3. The bottom portion 4312(2) of the caulked portion 431(2) is disposed between the inclined portion 4311T(2) and the inclined portion 4311B(2) in the axial direction.

An angle AGα(2) is an angle between the inclined portion 4311(2) and the bottom portion 4312(2) of the caulked portion 431(2) gripped by the gripping member 10. In particular, the angle AGα(2) is an angle between the inclined portion 4311(2) and the bottom portion 4312(2) when the inclined portion 4311(2) has a tapered shape. Specifically, the angle AGα(2) is an angle between the inclined portion 4311(2) and a plane obtained by extending the bottom portion 4312(2) to the side of the inclined portion 4311(2). In the gas sensor 1, when the inclined portion 4311(2) of the caulked portion 431(2) gripped by the gripping member 10 has a tapered shape, the angle AGα(2) of the inclined portion 4311(2) is 30° or more. In the example shown in FIG. 3, the inclined portion 4311B(2) on the rear end side of the caulked portion 431(2) is configured in a tapered shape. Therefore, the angle AGα(2) between the inclined portion 4311B(2) and the plane obtained by extending the bottom portion 4312(2) toward the side of the inclined portion 4311B(2) is 30° or more.

An angle AGβ(2) is an angle between the inclined portion 4311(2) and the bottom portion 4312(2) of the caulked portion 431(2) gripped by the gripping member 10 similarly to the angle AGα(2). In particular, the angle AGβ(2) is an angle between the inclined portion 4311(2) and the bottom portion 4312(2) when the inclined portion 4311(2) has a rounded shape. Specifically, the angle AGβ(2) is an angle between a plane parallel to a tangent of the inclined portion 4311(2) at a contact point between the inclined portion 4311(2) and the bottom portion 4312(2) and a plane obtained by extending the bottom portion 4312(2) toward the side of the inclined portion 4311(2). In the gas sensor 1, when the inclined portion 4311(2) of the caulked portion 431(2) gripped by the gripping member 10 has a rounded shape, the angle AGβ(2) of the inclined portion 4311(2) is 30° or more. In the example shown in FIG. 3, the inclined portion 4311T(2) on the front end side of the caulked portion 431(2) is configured in a rounded shape. Therefore, the angle AGβ(2) between the plane parallel to the tangent of the inclined portion 4311T(2) at the contact point between the inclined portion 4311T(2) and the bottom portion 4312(2), and the plane obtained by extending the bottom portion 4312(2) toward the side of the inclined portion 4311T(2) is 30° or more.

As described above, each of the two inclined portions 4311 (in the example shown in FIG. 2, the inclined portion 4311T(2) on the front end side and the inclined portion 4311B(2) on the rear end side) included in the caulked portion 431 gripped by the gripping member 10 (in the example shown in FIG. 2, the caulked portion 431(2)) satisfies a condition (A) or a condition (B) below. The condition (A) is "an angle AG(α) between the inclined portion 4311 and the plane obtained by extending the bottom portion 4312 towards the side of the inclined portion 4311 is 30° or more and less than 90°". The condition (B) is "an angle AG(β) between the plane parallel to the tangent of the inclined portion 4311 at the contact point between the inclined portion 4311 and the bottom portion 4312 and the plane obtained by extending the bottom portion 4312 toward the side of the inclined portion 4311 is 30° or more and less than 90°". For example, when the inclined portion 4311 has a tapered shape, the inclined portion 4311 satisfies the condition (A). For example, when the inclined portion 4311 has a rounded shape, the inclined portion 4311 satisfies the condition (B).

In the gas sensor 1, the gripping member 10 grips the outer peripheral surface covered with the tube 70 of the caulked portion 431 closest to the open end 43a of the cylindrical body 40 in the axial direction among the one or more caulked portions 431 (hereinafter, also referred to as a "rear end-side caulked portion"). The "rear end-side caulked portion" is, for example, the caulked portion 431(2) illustrated in FIG. 2. Unlike the gripping member 10 of the conventional gas sensor CS that grips the "portion covered with the tube 70 of the cylindrical body 40 where the caulked portion is not formed", the gripping member 10 of the gas sensor 1 grips the outer peripheral surface of the rear end-side caulked portion covered with the tube 70. The present inventors conducted an experiment, and confirmed that the gripping member 10 that grips the outer peripheral surface covered with the tube 70 of the rear end-side caulked portion is less likely to move even when an impact is applied, as compared with the gripping member 10 of the conventional gas sensor CS. Therefore, the gas sensor 1 exerts an effect that the possibility can be suppressed that the position (gripping position) of the gripping member 10 is moved by an external impact and the gripping force of the gripping member 10 is reduced.

In addition, in the gas sensor 1, the angle AG (the angles AG(α), the AG(β)) between the inclined portion 4311 and the bottom portion 4312 of the rear end-side caulked portion satisfies the above-described condition (A) or (B). For example, when at least one of the two inclined portions 4311(2) (the inclined portion 4311T(2) and the inclined portion 4311B(2)) of the caulked portion 431(2) gripped by the gripping member 10 has a tapered shape, the tapered inclined portion 4311(2) satisfies the condition (A). For example, when at least one of the two inclined portions 4311(2) (the inclined portion 4311T(2) and the inclined portion 4311B(2)) of the caulked portion 431(2) gripped by the gripping member 10 has a rounded shape, the rounded inclined portion 4311(2) satisfies the condition (B).

The present inventors conducted an experiment to identify a desirable range of the angle of the inclined portion 4311 of the rear end-side caulked portion gripped by the gripping member 10. As a result, it has been confirmed that when the inclined portion 4311 has a tapered shape, that is, when the inclined portion 4311 is formed so as to have a straight line in the cross section parallel to the longitudinal axis of the gas sensor (cylindrical body 40) and in contact with the axis, the angle of the inclined portion 4311 is desirably within a range below. That is, the present inventors have confirmed that it is desirable to set the angle AG(α) between the inclined portion 4311 and the plane obtained by extending the bottom portion 4312 toward the side of the inclined portion 4311 to 30° or more. In addition, since the inclined portion 4311 is the portion where the diameter of the cylindrical body 40 continuously changes along the axial direction of the cylindrical body 40, the angle AG(α) is less than 90°.

In addition, the present inventors have confirmed that, when the inclined portion 4311 has a rounded shape, that is, when the inclined portion 4311 is formed so as to have a curved line in the cross section parallel to the longitudinal axis of the gas sensor (cylindrical body 40) and in contact with the axis, it is desirable to set the angle of the inclined portion 4311 within a range below. That is, the present inventors have confirmed that it is desirable to set, to 30° or more, the angle AG(β) between the plane parallel to the tangent of the inclined portion 4311 at the contact point between the inclined portion 4311 and the bottom portion 4312, and the plane obtained by extending the bottom portion 4312 toward the side of the inclined portion 4311. In addition, similarly to the angle AG(α), the angle AG(β) is also less than 90°.

The present inventors have experimentally confirmed that when the inclined portion 4311 has a tapered shape, the gripping position of the gripping member 10 can be reliably fixed by the inclined portion 4311 by setting the angle AG(α) to 30° or more and less than 90°. In addition, the present inventors have experimentally confirmed that when the inclined portion 4311 has a rounded shape, the gripping position of the gripping member 10 can be reliably fixed by the inclined portion 4311 by setting the angle AG(β) to 30° or more and less than 90°. When each of the angle AG(α) and the angle AG(β) is set to less than 30°, the position of the gripping member 10 (gripping position) cannot be reliably fixed by the inclined portion 4311 of the rear end-side caulked portion, and the gripping position of the gripping member 10 is easily moved (easily displaced) by an external impact, and the gripping force is reduced.

Therefore, the angle AG(α) of the inclined portion 4311 is set to 30° or more and less than 90°, or the angle AG(β) is set to 30° or more and less than 90°, whereby the gas sensor 1 exerts the effect below. That is, the gas sensor 1 exerts the effect that the gripping position of the gripping member 10 can be reliably fixed by the inclined portion 4311 of the rear end-side caulked portion.

As described above, each of the two inclined portions 4311 (in the example shown in FIG. 2, the inclined portion 4311T(2) on the front end side and the inclined portion 4311B(2) on the rear end side) included in the caulked portion 431 gripped by the gripping member 10 (in the example shown in FIGS. 1 to 3, the caulked portion 431(2)) satisfies the above-described condition (A) or condition (B). For example, when at least one of the inclined portion 4311T(2) on the front end side and the inclined portion 4311B(2) on the rear end side has a tapered shape, at least one of the inclined portion 4311T(2) and the inclined portion 4311B(2) having the tapered shape satisfies the condition (A). For example, when at least one of the inclined portion 4311T(2) and the inclined portion 4311B(2) has a rounded shape, at least one of the inclined portion 4311T(2) and the inclined portion 4311B(2) having the rounded shape satisfies the condition (B). Since each of the two inclined portions 4311 of the caulked portion 431 gripped by the gripping member 10 satisfy the condition (A) or the condition (B), the caulked portion 431 prevents the position (gripping position) of the gripping member 10 from moving and suppresses reduction in the gripping force of the gripping member 10. In addition, in order to maintain and improve the gripping force of the gripping member 10, the axial length La of the gripping member 10 (in the axial direction of the cylindrical body 40) is desirably equal to or less than the axial length Lb(2) of the caulked portion 431(2) gripped by the gripping member 10. Furthermore, in order to maintain and improve the gripping force of the gripping member 10, the diameter $\Phi d$ of the portion of the cylindrical body 40 where the caulked portion 431 is not formed is desirably larger by 0.5 mm or more than the diameter $\Phi c(2)$ of the cylindrical body 40 at the bottom portion 4312(2) of the caulked portion 431(2).

On the other hand, of the one or more caulked portions 431 formed on the side where the open end 43a of the cylindrical body 40 is formed, the caulked portion 431 that is not gripped by the gripping member 10 may not have the above-described configuration. For example, each of the two inclined portions 4311 (in the example shown in FIG. 2, the inclined portion 4311T(1) on the front end side and the inclined portion 4311B(1) on the rear end side) included in the caulked portion 431(1) may not satisfy any of the above-described conditions (A) and (B). The axial length La of the gripping member 10 (in the axial direction of the cylindrical body 40) may be larger than an axial length Lb(1) of the caulked portion 431(1) not gripped by the gripping member 10. Furthermore, a difference between the diameter $\Phi d$ of the portion of the cylindrical body 40 where the caulked portion 431 is not formed and a diameter $@c(1)$ of the cylindrical body 40 at the bottom portion 4312(1) of the caulked portion 431(1) may be less than 0.5 mm. The caulked portion 431 not gripped by the gripping member 10 (in the example shown in FIGS. 1 to 3, the caulked portion 431(1)) may have a configuration similar to that of a conventional general caulked portion. In addition, the caulked portion 431 not gripped by the gripping member 10 may have a configuration similar to the caulked portion 431 gripped by the gripping member 10 (in the example shown in FIGS. 1 to 3, the caulked portion 431(2)).

(Rear-End Outer Peripheral Surface of Cylindrical Body)

Figures 4A, 4B:
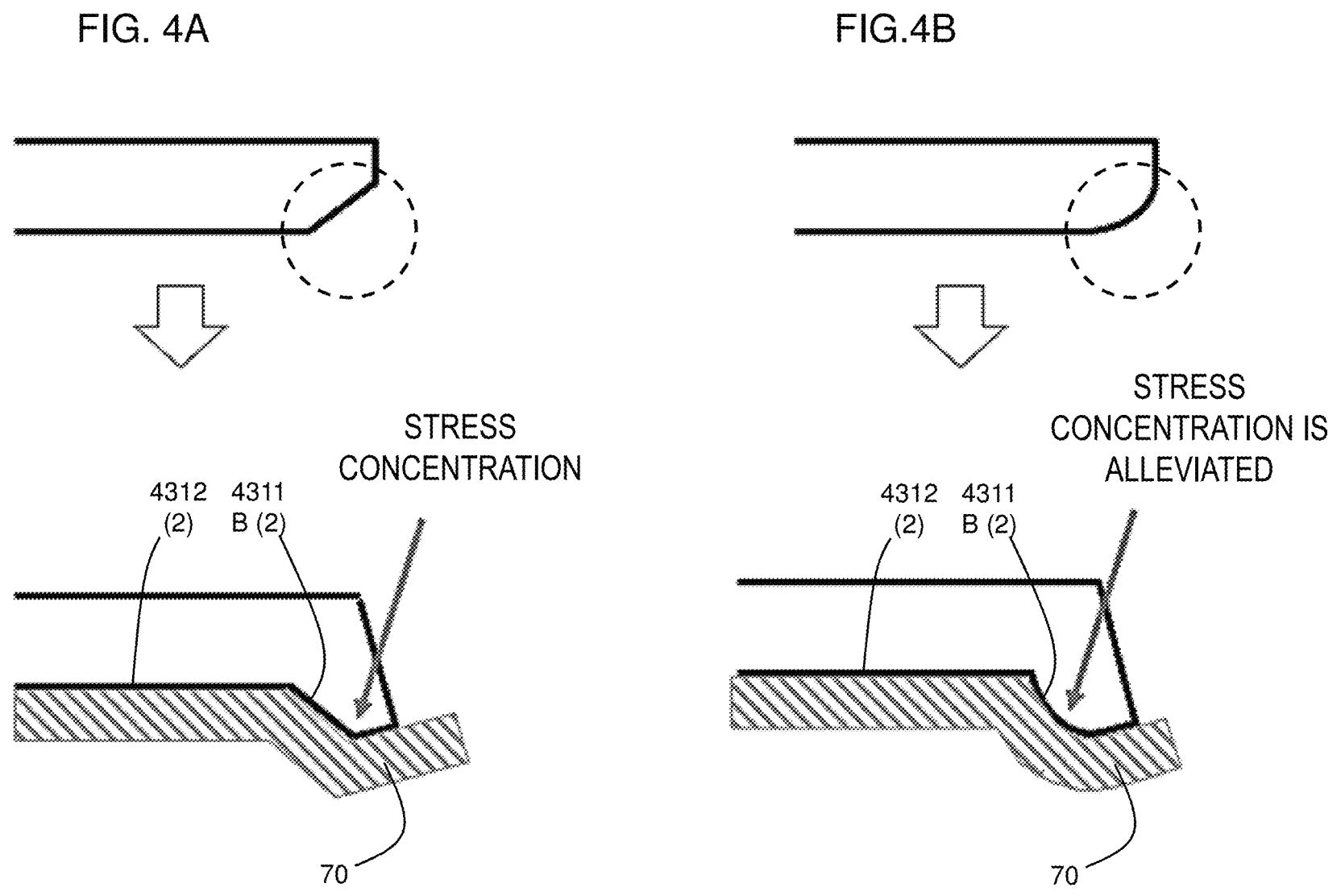

FIG. 4 is a diagram showing comparison between a case where the outer peripheral surface of the rear end (open end 43a) of the cylindrical body 40 included in the gas sensor 1 is not subjected to round chamfering and a case where the outer peripheral surface is subjected to round chamfering. Specifically, FIG. 4A schematically shows a configuration of a cross section of the "rear-end outer peripheral surface of the cylindrical body 40 not subjected to the round chamfering", the cross section being parallel to and in contact with the longitudinal axis (the axis line, the line along the left-right direction in the drawing) of the gas sensor 1 (the cylindrical body 40). In addition, FIG. 4B schematically shows a configuration of a cross section of a "rear-end outer peripheral surface of the cylindrical body 40 subjected to the round chamfering", the cross section being parallel to and in contact with the longitudinal axis (the axis line, the line along the left-right direction in the drawing) of the gas sensor 1 (the cylindrical body 40). In each of the examples of FIGS. 4A and 4B, a left direction in the drawing is the front end side of the gas sensor 1, and a right direction in the drawing is the rear end side of the gas sensor 1. FIGS. 4A and 4B show the case where the rear-end outer peripheral surface of the cylindrical body 40 on a lower side in the drawing of FIG. 2 with respect to the longitudinal axis of the gas sensor 1 (the cylindrical body 40) is not subjected to the round chamfering, and the case where the rear-end outer peripheral surface is subjected to the round chamfering.

As illustrated in FIG. 4A, when the outer peripheral surface of the rear end (open end 43a) of the cylindrical body 40 is not subjected to the round chamfering, a corner at the rear end of the outer peripheral surface of the cylindrical body 40 comes into contact with the tube 70, a stress is concentrated on the corner (the contact position), and the tube 70 is easily broken. In an example shown in FIG. 4 (A), the inclined portion 4311B(2) of the caulked portion 431(2) is formed in a tapered shape, and an end portion on a rear end side (the rear end portion) of the inclined portion 4311B(2) is formed in a corner shape. The tube 70 is in contact with the rear end portion of the inclined portion 4311B(2) having the corner shape. Therefore, for example, when a tension is applied to the tube 70 so as to pull the tube 70 in the axial direction (the right direction in FIG. 4), the tube 70 is easily broken from the contact position with the rear end portion of the inclined portion 4311B(2).

As illustrated in FIG. 4B, when the outer peripheral surface of the rear end (the open end 43a) of the cylindrical body 40 is subjected to the round chamfering, that is, when the outer peripheral surface of the cylindrical body 40 at the open end 43a is subjected to the round chamfering, stress concentration can be alleviated as compared with the configuration illustrated in FIG. 4A. Therefore, by subjecting the outer peripheral surface of the rear end of the cylindrical body 40 to the round chamfering, a possibility that the tube 70 is broken can be suppressed. For example, in the example shown in FIG. 4B, the inclined portion 4311B(2) on the rear end side of the caulked portion 431(2) is formed in a rounded shape. Specifically, in (B) of FIG. 4, the inclined portion 4311B(2) of the caulked portion 431(2) is formed so as to have a rounded shape, that is, a curved line (curved shape) in the cross section parallel to and in contact with the longitudinal axis of the gas sensor. Therefore, in the example illustrated in (B) of FIG. 4, the end portion on the rear end side (the rear end portion) of the inclined portion 4311B(2) has a smooth curved shape unlike (A) of FIG. 4. Therefore, for example, even when a tension is applied to the tube 70 so as to pull the tube 70 in the axial direction (the right direction in FIG. 4), there is a low possibility that the tube 70 is broken from the contact position with the rear end portion of the inclined portion 4311B(2).

As described above, in the gas sensor 1, the outer peripheral surface of the cylindrical body 40 at the open end 43a may be subjected to the round chamfering. That is, the outer peripheral surface of the cylindrical body 40 at the open end 43a may have a rounded shape, that is, may be formed so as to have a curved line (a curved shape) in the cross section parallel to and in contact with the axis (the axis in the longitudinal direction) of the cylindrical by 40. For example, a thickness of the cylindrical body 40 may continuously decrease so as to decrease toward the open end 43a along the axis of the cylindrical body 40, and the rear-end outer peripheral surface of the cylindrical body 40 may have a curved shape without a corner in the cross section. The present inventors have experimentally confirmed that the possibility of breakage of the tube 70 can be suppressed by subjecting the outer peripheral surface of the cylindrical body 40 at the open end 43a to the round chamfering. When the outer peripheral surface of the cylindrical body 40 at the open end 43a is not subjected to the round chamfering, the corner of the outer peripheral surface of the cylindrical body 40 at the open end 43a comes into contact with the tube 70 disposed between the gripping member 10 and the cylindrical body 40, and a stress is concentrated at the contact position, so that the tube 70 is easily broken. By subjecting the outer peripheral surface of the cylindrical body 40 at the open end 43a to the round chamfering, stress concentration can be alleviated, and the possibility that the tube 70 is broken can be suppressed. Therefore, by subjecting the outer peripheral surface of the cylindrical body 40 at the open end 43a to the round chamfering, the gas sensor 1 exerts the effect that the possibility that the tube 70 is broken can be suppressed.

[Features]

As described above, the gas sensor 1 according to the one aspect of the present invention includes the sensor element 20, the cylindrical body 40, the lead wires 80, the tube 70, and the gripping member 10. The cylindrical body 40 is a cylindrical member in which the sensor element 20 is disposed thereinside and the open end 43a is formed. The lead wires 80 are electrically connected to the sensor element 20 and extend outward from the inside of the cylindrical body 40 through the open end 43a. The tube 70 covers the outer peripheral surface of the end portion of the cylindrical body 40 including the open end 43a and the portions of the lead wires 80 extending outward from the open end 43a of the cylindrical body 40. The gripping member 10 grips the portion of the outer peripheral surface covered with the tube 70 of the cylindrical body 40 such that the tube 70 protrudes to the side opposite to the open end 43a of the cylindrical body 40. In the gas sensor 1, the one or more caulked portions 431 are formed on the side where the open end 43a of the cylindrical body 40 is formed. The one or more caulked portions 431 each include the two inclined portions 4311 and the bottom portion 4312. Each of the two inclined portions 4311 of each of the caulked portions 431 is a portion where the diameter of the cylindrical body 40 continuously changes along the axial direction of the cylindrical body 40. The two inclined portions 4311 are each formed in, for example, a tapered shape or a rounded shape. The bottom portion 4312 of the caulked portion 431 is a portion that is disposed between the two inclined portions 4311 in the axial direction of the cylindrical body 40 and has the constant diameter of the cylindrical body 40 along the axial direction.

In the gas sensor 1, the gripping member 10 grips the outer peripheral surface covered with the tube 70 of the caulked portion 431 closest to the open end 43a of the cylindrical body 40 in the axial direction of the cylindrical body 40 among the one or more caulked portions 431. For example, in the example shown in FIG. 2, the gripping member 10 grips the outer peripheral surface covered with the tube 70 of the caulked portion 431(2) close to the open end 43a among the caulked portion 431(1) on the front end side and the caulked portion 431(2) on the rear end side in the axial direction.

Each of the two inclined portions 4311 (in the example shown in FIG. 2, the inclined portion 4311T(2) on the front end side and the inclined portion 4311B(2) on the rear end side) included in the caulked portion 431 gripped by the gripping member 10 (in the example shown in FIG. 2, the caulked portion 431(2)) satisfies the condition (A) or the condition (B) below. The condition (A) is "the angle AG($\alpha$) between the inclined portion 4311 and the plane obtained by extending the bottom portion 4312 towards the side of the inclined portion 4311 is 30° or more and less than 90°". The condition (B) is "the angle AG($\beta$) between the plane parallel to the tangent of the inclined portion 4311 at the contact point between the inclined portion 4311 and the bottom portion 4312 and the plane obtained by extending the bottom portion 4312 toward the side of the inclined portion 4311 is 30° or more and less than 90°". For example, when the inclined portion 4311 has a tapered shape, the inclined portion 4311 satisfies the condition (A). For example, when the inclined portion 4311 has a rounded shape, the inclined portion 4311 satisfies the condition (B).

In the configuration, in the gas sensor 1, the gripping member 10 grips the outer peripheral surface covered with the tube 70 of the caulked portion 431 closest to the open end 43a of the cylindrical body 40 in the axial direction (hereinafter, also referred to as the "rear end-side caulked portion") among the one or more caulked portions 431. The "rear end-side caulked portion" is, for example, the caulked portion 431(2) illustrated in FIG. 2. Unlike the gripping member 10 of the conventional gas sensor CS that grips the "portion covered with the tube 70 of the cylindrical body 40 where the caulked portion is not formed", the gripping member 10 of the gas sensor 1 grips the outer peripheral surface of the rear end-side caulked portion covered with the tube 70. The present inventors conducted an experiment, and confirmed that the gripping member 10 that grips the outer peripheral surface covered with the tube 70 of the rear end-side caulked portion is less likely to move even when an impact is applied, as compared with the gripping member 10 of the conventional gas sensor CS. Therefore, the gas sensor 1 exerts an effect that the possibility can be suppressed that the position (gripping position) of the gripping member 10 is moved by an external impact and the gripping force of the gripping member 10 is reduced.

In addition, in the gas sensor 1, the angle AG (the angles AG($\alpha$), the AG($\beta$)) between the inclined portion 4311 and the bottom portion 4312 of the rear end-side caulked portion satisfies the above-described condition (A) or condition (B).

The present inventors further conducted an experiment to identify the desirable range of the angle of each of the inclined portions 4311 of the rear end-side caulked portion. As a result, it has been confirmed that when the inclined portion 4311 has a tapered shape, that is, when the inclined portion 4311 is formed so as to have a straight line in the cross section parallel to the longitudinal axis of the gas sensor 1 (cylindrical body 40) and in contact with the axis, the angle of the inclined portion 4311 is desirably within a range below. That is, the present inventors have confirmed that it is desirable to set the angle AG($\alpha$) between the inclined portion 4311 and the plane obtained by extending the bottom portion 4312 toward the side of the inclined portion 4311 to 30° or more. In addition, since the inclined portion 4311 is the portion where the diameter of the cylindrical body 40 continuously changes along the axial direction of the cylindrical body 40, the angle AG($\alpha$) is less than 90°.

In addition, the present inventors have confirmed that, when the inclined portion 4311 has a rounded shape, that is, when the inclined portion 4311 is formed so as to have a curved line in the cross section parallel to the longitudinal axis of the gas sensor (cylindrical body 40) and in contact with the axis, it is desirable to set the angle of the inclined portion 4311 within a range below. That is, the present inventors have confirmed that it is desirable to set, to 30° or more, the angle AG($\beta$) between the plane parallel to the tangent of the inclined portion 4311 at the contact point between the inclined portion 4311 and the bottom portion 4312, and the plane obtained by extending the bottom portion 4312 toward the side of the inclined portion 4311. In addition, similarly to the angle AG($\alpha$), the angle AG($\beta$) is also less than 90°.

The present inventors have experimentally confirmed that when the inclined portion 4311 has a tapered shape, the gripping position of the gripping member 10 can be reliably fixed by the inclined portion 4311 by setting the angle AG($\alpha$) to 30° or more and less than 90°. In addition, the present inventors have experimentally confirmed that when the inclined portion 4311 has a rounded shape, the gripping position of the gripping member 10 can be reliably fixed by the inclined portion 4311 by setting the angle AG($\beta$) to 30° or more and less than 90°. When each of the angle AG($\alpha$) and the angle AG($\beta$) is set to less than 30°, the position of the gripping member 10 (gripping position) cannot be reliably fixed by the inclined portion 4311 of the rear end-side caulked portion, and the gripping position of the gripping member 10 is easily moved (easily displaced) by an external impact, and the gripping force is reduced.

Therefore, the angle AG($\alpha$) of the inclined portion 4311 is set to 30° or more and less than 90°, or the angle AG($\beta$) is set to 30° or more and less than 90°, whereby the gas sensor 1 exerts the effect below. That is, the gas sensor 1 exerts the effect that the gripping position of the gripping member 10 can be reliably fixed by the inclined portion 4311 of the rear end-side caulked portion.

MODIFICATIONS

Although the embodiment of the present invention has been described above, the above description of the embodiment is merely an example of the present invention in all respects. Various improvements and modifications may be made to the above embodiment. With respect to each of the components of the above embodiment, omission, replacement, and addition of the component may be appropriately performed. In addition, the shape and dimension of each component of the above embodiment may be appropriately changed according to the embodiment. For example, modifications below are possible. Note that in description below, similar reference signs are used for similar components to those of the above embodiment, and description of similar points to those of the above embodiment is appropriately omitted. Modifications below can be appropriately combined.

(Number of Caulked Portions)

So far, the example has been described in which a number of the caulked portions 431 formed in the cylindrical body 40 is "two". However, in the gas sensor according to the present invention, the number of the caulked portions 431 formed in the cylindrical body 40 may be "one" or three or more. In the gas sensor according to the present invention, the number of the caulked portions 431 formed in the cylindrical body 40 may be appropriately determined in accordance with the length in the axial direction (longitudinal direction) of the gas sensor or the like.

For example, when the number of the caulked portions 431 formed in the cylindrical body 40 is "one", the gripping member 10 may grip the outer peripheral surface covered with the tube 70 of the "one" caulked portion 431. When the number of the caulked portions 431 formed in the cylindrical body 40 is "three" or more, the gripping member 10 may grip the outer peripheral surface covered with the tube 70 of the caulked portion 431 closest to the open end 43a in the axial direction of the gas sensor 1 among the "three" or more caulked portions 431.

(Configuration of Inclined Portion in Caulked Portion)

In the gas sensor according to the present invention, each of the two inclined portions 4311 of the caulked portion 431 may have a tapered shape or a rounded shape. One of the inclined portion 4311T on the front end side and the inclined portion 4311B on the rear end side may have a tapered shape, and the other may have a rounded shape. Both of the inclined portion 4311T on the front end side and the inclined portion 4311B on the rear end side may have a tapered shape, and both may have a rounded shape.

(Configuration of Gas Sensor)

As the gas sensor according to the one aspect of the present invention, the gas sensor 1 has been described that includes the gripping member 10, the sensor element 20, the protective cover 30, the cylindrical body 40, the connector 50, the elastic body 60, the tube 70, the lead wires 80, and the annular component 90. However, the gas sensor according to the one aspect of the present invention may include: (1) a sensor element; (2) a cylindrical body in which the sensor element is disposed thereinside and an open end is formed; (3) a lead wire electrically connected to the sensor element and extending outward from an inside of the cylindrical body through the open end of the cylindrical body; (4) a tube that covers an outer peripheral surface of an end portion of the cylindrical body including the open end and a portion of the lead wire extending outward from the open end of the cylindrical body; and (5) a gripping member that grips a portion of an outer peripheral surface of the cylindrical body covered with the tube such that the tube protrudes to a side opposite to the open end of the cylindrical body. It is not essential that the gas sensor according to the one aspect of the present invention includes, for example, the protective cover 30, the connector 50, the elastic body 60, and the annular component 90.

(Position of Gripping Member (Gripping Position))

So far, the example has been described in which the gripping member 10 grips the caulked portion 431 closest to the open end 43a of the cylindrical body 40 in the axial direction among the one or more caulked portions 431 formed on the rear end side of the cylindrical body 40. However, the gripping member 10 may grip the caulked portion 431 other than the "caulked portion 431 closest to the open end 43a of the cylindrical body 40 in the axial direction" among the one or more caulked portions 431. In the example shown in FIG. 2, the gripping member 10 grips the outer peripheral surface covered with the tube 70 of the caulked portion 431(2) among the caulked portion 431(1) on the front end side and the caulked portion 431(2) on the rear end side. However, the gripping member 10 may grip the outer peripheral surface of the caulked portion 431(1) covered with the tube 70. In that case, the caulked portion 431(1) desirably has the configuration described for the caulked portion 431(2). However, when the gripping member 10 grips the caulked portion 431 on the most rear end side among the one or more caulked portions 431, the gas sensor 1 can effectively prevent the breakage of the tube 70 by forming the outer peripheral surface of the open end 43a of the cylindrical body 40 in a rounded shape.

EXAMPLES

In order to verify the effect of the present invention, gas sensors according to Comparative Example 1 and Examples 1 to 4 below were produced. However, the present invention is not limited to the following examples.

tapered shape, an angle between the inclined portion 4311T(2) and a plane obtained by extending the bottom portion

TABLE 1

| | Gripping position | La/Lb (2) | AGα (2) | AGβ (2) | Φd-Φc (2) | Round chamfering | Evaluation 1 |
|---|---|---|---|---|---|---|---|
| Comparative Example 1 | Portion where caulked portion is not formed | — | — | — | 0.8 | Present | 1 |
| Example 1 | Caulked portion on rear end side | 0.88 | 35 | 55 | 0.8 | Present | 1.27 |

TABLE 2

| | Gripping position | La/Lb (2) | AGα (2) | AGβ (2) | Φd-Φc (2) | Round chamfering | Evaluation 2 | Evaluation 3 |
|---|---|---|---|---|---|---|---|---|
| Example 1 | Caulked portion on rear end side | 0.88 | 35 | 55 | 0.8 | Present | ○ | 1 |
| Example 2 | Caulked portion on rear end side | 2.06 | 35 | 55 | 0.8 | Absent | ○ | 0.34 |
| Example 3 | Caulked portion on rear end side | 0.88 | 20 | 55 | 0.8 | Absent | X | — |
| Example 4 | Caulked portion on rear end side | 0.88 | 35 | 55 | 0.8 | Absent | ○ | 0.61 |

Table 1 is a table in which Experiment 1 of applying an impact to the gripping member 10 (for example, an impact was applied to the gripping member 10 along the axial direction (longitudinal direction) of the gas sensor) was conducted for each of the gas sensors according to each of Comparative Example 1 and Example 1, and results of Experiment 1 were organized.

Comparative Example 1 is the conventional gas sensor CS as illustrated in FIG. 5. Example 1 is the gas sensor 1 described with reference to FIGS. 1 to 4. Comparative Example 1 and Example 1 have a same configuration except for a disposition position of the gripping member 10.

In Comparative Example 1, the gripping member 10 is disposed at the crest portion 439 in FIG. 5. That is, in Comparative Example 1, the gripping member 10 grips an outer peripheral surface covered with the tube 70 of the cylindrical body 40, that is, an outer peripheral surface of the crest portion 439 covered with the tube 70. As described before, the crest portion 439 is a portion other than a portion where the caulked portion 431 is formed on the rear end side of the cylindrical body 40, and can also be regarded as a portion where the caulked portion 431 is not formed. For example, in Comparative Example 1, the gripping member 10 grips the outer peripheral surface of the crest portion 439 between the caulked portion 431(1) and the caulked portion 431(2).

In Comparative Example 1, since the gripping member 10 is disposed on the crest portion 439, a value (La/Lb(2)) obtained by dividing an axial length La of the gripping member 10 by an axial length Lb(2) of the caulked portion 431(2) was set to "–". Similarly, in Comparative Example 1, each of an angle AGα(2) and an angle AGβ(2) was set to "–". The angle AGα(2) is an angle between a tapered inclined portion 4311(2) and a plane obtained by extending a bottom portion 4312(2) toward a side of the inclined portion 4311(2) when the inclined portion 4311(2) of a caulked portion 431(2) has a tapered shape. For example, when an inclined portion 4311T(2) on the front end side in the axial direction of the caulked portion 431(2) has a 4312(2) toward a side of the inclined portion 4311T(2) is the angle AGα(2). The angle AGβ(2) is an angle of a tangent of the inclined portion 4311(2) at a contact point between the rounded-shaped inclined portion 4311(2) and the bottom portion 4312(2) when the inclined portion 4311(2) of the caulked portion 431(2) has a rounded shape. More exactly, the angle AGβ(2) is an angle between a plane parallel to the tangent of the inclined portion 4311(2) at the above-described contact point and the plane obtained by extending the bottom portion 4312(2) toward the side of the inclined portion 4311(2). For example, when an inclined portion 4311B(2) on the rear end side in the axial direction of the caulked portion 431(2) has a rounded shape, an angle of a tangent of the inclined portion 4311B(2) at a contact point between the inclined portion 4311B(2) and the bottom portion 4312(2) is the angle AGβ(2).

Φd is a diameter of the portion of the cylindrical body 40 where the caulked portion 431 is not formed, and is a diameter of the cylindrical body 40 at the crest portion 439 in the example shown in FIG. 5. Φc is a diameter of the cylindrical body 40 at the caulked portion 431. Φc(2) is a diameter of the cylindrical body 40 at the bottom portion 4312(2) of the caulked portion 431(2) closest to the open end 43a in the axial direction of the gas sensor among the caulked portion 431(1) and the caulked portion 431(2). In Comparative Example 1, a difference (Φd–Φc(2)) between Φd and Φc(2) is "0.8".

In Comparative Example 1, an outer peripheral surface of the rear end of the cylindrical body 40 is subjected to round chamfering, that is, the round chamfering is "present".

In Example 1, the gripping member 10 is disposed in the caulked portion 431, and is particularly disposed in the caulked portion 431(2) closest to the open end 43a in the axial direction of the gas sensor among the caulked portion 431(1) and the caulked portion 431(2). That is, in Example 1, the gripping member 10 grips the outer peripheral surface covered with the tube 70 of the caulked portion 431(2). That is, in Example 1, the gripping member 10 grips the outer peripheral surface covered with the tube 70 of the caulked portion 431(2) on the most rear end side among the caulked portion 431(1) and the caulked portion 431(2).

In Example 1, the value (La/Lb(2)) obtained by dividing the axial length La of the gripping member 10 by the axial length Lb(2) of the caulked portion 431(2) is "0.88". In addition, in Example 1, the angle AGα(2) is "35°", and the angle AGβ(2) is "55°". In the following description, a unit "0" of the angle is omitted. For example, as illustrated in FIG. 3, in Example 1, the inclined portion 4311T(2) on the front end side in the axial direction of the caulked portion 431(2) is formed so as to have a rounded shape, that is, a curved line in the cross section parallel to the axis and in contact with the axis. The angle AGβ(2) between the plane parallel to the tangent of the inclined portion 4311T(2) at the contact point between the inclined portion 4311T(2) and the bottom portion 4312(2), and the plane obtained by extending the bottom portion 4312(2) toward the side of the inclined portion 4311T(2) is "55". In addition, in Example 1, the inclined portion 4311B(2) on the rear end side in the axial direction of the caulked portion 431(2) is formed so as to have a tapered shape, that is, a straight line in the cross section parallel to the axis and in contact with the axis. In addition, the angle AGα(2) between the inclined portion 4311B(2) and the plane obtained by extending the bottom portion 4312(2) towards the side of the inclined portion 4311B(2) is "35".

In Example 1, the difference (Φd–Φc(2)) between the diameter Φd of the portion of the cylindrical body 40 where the caulked portion 431 is not formed and the diameter Φc(2) of the cylindrical body 40 at the bottom portion 4312(2) of the caulked portion 431(2) is "0.8".

In Example 1, the outer peripheral surface of the rear end of the cylindrical body 40 is subjected to the round chamfering, that is, the round chamfering is "present".

A weight was dropped on each of the gripping members 10 of Comparative Example 1 and Example 1 (for example, the weight is dropped so that an impact in the axial direction of the gas sensor is applied to the gripping member 10), and it was confirmed whether the gripping member 10 had not been displaced (moved). When the gripping member 10 did not move, a drop height of the weight was gradually increased, and the drop height of the weight was increased until the gripping member 10 moved. Then, the drop height when the gripping member 10 was moved (displaced) (a limit drop height) was compared between Comparative Example 1 and Example 1. "Evaluation 1" in Table 1 indicates how many times of the limit drop height in Comparative Example 1 the limit drop height in Example 1 was, where the drop height (limit drop height) when the gripping member 10 moved in Comparative Example 1 was "1".

In Experiment 1, it has been confirmed that in Example 1, the gripping member 10 was less likely to move even when an external impact was applied, as compared with Comparative Example 1. Specifically, in Example 1, it has been confirmed that the gripping member 10 was less likely to move "1.27" times of Comparative Example 1 even when an external impact is applied to the gripping member 10.

Table 2 is a table in which Experiment 2 of pulling the tube 70 was conducted on the gas sensor according to each of Examples 1 to 4, and results of Experiment 2 were organized.

The gas sensor according to each of Examples 1 to 4 includes members similar to those of the gas sensor 1 described with reference to FIGS. 1 to 4. In particular, Examples 1 to 4 are common in that the gripping member 10 is disposed in the caulked portion 431(2) closest to the open end 43a in the axial direction of the gas sensor among the caulked portion 431(1) and the caulked portion 431(2). However, Examples 1 to 4 are different in three points below.

Firstly, in each of Examples 1, 3, and 4, the value (La/Lb(2)) obtained by dividing the axial length La of the gripping member 10 by the axial length Lb(2) of the caulked portion 431(2) is "0.88". That is, in each of Examples 1, 3, and 4, the axial length La of the gripping member 10 is equal to or less than the axial length Lb(2) of the caulked portion 431(2). On the other hand, in Example 2, the value (La/Lb(2)) obtained by dividing the axial length La of the gripping member 10 by the axial length Lb(2) of the caulked portion 431(2) is "2.06". That is, in Example 2, the axial length La of the gripping member 10 is longer than the axial length Lb(2) of the caulked portion 431(2).

Secondly, in each of Examples 1, 2 and 4, the angle AGα(2) is "35", that is, the angle AGα(2) is "30" or more. On the other hand, in Example 3, the angle AGα(2) is "20", that is, the angle AGα(2) is less than "30".

Thirdly, in Example 1, the outer peripheral surface of the rear end of the cylindrical body 40 is subjected to the round chamfering, that is, the round chamfering is "present". On the other hand, in each of Examples 2, 3, and 4, the outer peripheral surface of the rear end of the cylindrical body 40 is not subjected to the round chamfering, that is, the round chamfering is "absent".

Experiment 2 in which the tube 70 was pulled until breakage of the tube 70 or movement (displacement) of the gripping member 10 occurred was conducted for each of Examples 1 to 4. Specifically, for each of Examples, Experiment 2 described above was conducted on a plurality of gas sensors according to each of Examples.

As a result of Experiment 2, for Example in which in all of the plurality of gas sensors according to the relevant Example, "breakage of the tube 70" was caused instead of "movement of the gripping member 10", "Evaluation 2" in Table 2 was set to "○ (good)". As a result of Experiment 2, for Example in which in all of the plurality of gas sensors according to the relevant Example, the "movement of the gripping member 10" was caused instead of the "breakage of the tube 70", "Evaluation 2" in Table 2 was set to "x (bad)". This indicates that the gas sensor in which the "breakage of the tube 70" was caused instead of the "movement of the gripping member 10" can grip the tube 70 (and the cylindrical body 40) with a sufficient gripping force by the gripping member 10.

Furthermore, with respect to Examples 1, 2, and 4 in which "Evaluation 2" in Table 2 was "○", a magnitude of a tensile load when the "breakage of the tube 70" was caused was evaluated (Evaluation 3). Specifically, in Example 1, the magnitude of the tensile load (limit load) when the "breakage of the tube 70" was caused was set to "1". Then, for each of Examples 2 and 4, how many times of the limit load in Example 1 the limit load was.

Examples 1 and 3 have similar configurations except that the angle AGα(2) is "30" or more, or less than "30". Evaluation 2 of Example 1 was "○", that is, the "movement of the gripping member 10" was not caused in Example 1. In contrast, Evaluation 2 of Example 3 was "x", that is, the "movement of the gripping member 10" was caused in Example 3. Therefore, it has been confirmed that when the angle AGα(2) is less than 30, the position of the gripping member 10 cannot be reliably fixed by the inclined portion 4311(2) of the caulked portion 431(2), the position of the gripping member 10 is easily moved, and the gripping force of the gripping member 10 is reduced. That is, it has been confirmed that by setting the angle AGα(2) to 30 or more, the position of the gripping member 10 can be reliably fixed by the inclined portion 4311(2) of the caulked portion 431(2), and the displacement of the gripping member 10 and the reduction in the gripping force can be avoided.

Examples 1 and 2 have similar configurations except that the axial length La of the gripping member 10 is equal to or less than the axial length Lb(2) of the caulked portion 431(2) or longer than the axial length Lb(2) of the caulked portion 431(2). In Evaluation 3, when the limit load of Example 1 is "1", the limit load of Example 2 is "0.34", and in Example 2, the limit load is significantly reduced as compared with Example 1, that is, the gripping force of the gripping member 10 is reduced. Therefore, it has been confirmed that the gripping force of the gripping member 10 can be improved by setting the axial length La of the gripping member 10 to be equal to or less than the axial length Lb(2) of the caulked portion 431(2).

Examples 1 and 4 have similar configurations except that the outer peripheral surface of the rear end of the cylindrical body 40 is subjected to the round chamfering or not. In Evaluation 3, when the limit load of Example 1 is "1", the limit load of Example 4 is "0.61". That is, it was confirmed that the "breakage of the tube 70" was easily caused in Example 4 as compared with Example 1. When the outer peripheral surface of the rear end of the cylindrical body 40 is not subjected to the round chamfering, the corner at the rear end of the outer peripheral surface of the cylindrical body 40 comes into contact with the tube 70 disposed between the gripping member 10 and the cylindrical body 40, and a stress is concentrated at the contact position, so that the tube 70 is easily broken. Therefore, it was confirmed that by subjecting the outer peripheral surface of the rear end of the cylindrical body 40 to the round chamfering, the possibility that the tube 70 was broken could be suppressed.

REFERENCE SIGNS LIST

1 Gas sensor
20 Sensor element
40 Cylindrical body
43*a* Open end
431 Caulked portion
4311 Inclined portion
4312 Bottom portion
80 Lead wire
70 Tube
10 Gripping member
AG Angle
The invention claimed is:
1. A gas sensor comprising:
a sensor element;
a cylindrical body in which the sensor element is disposed thereinside and an open end is formed;
a lead wire that is electrically connected to the sensor element and extends outward from the inside of the cylindrical body through the open end;

a tube that covers an outer peripheral surface of an end portion of the cylindrical body including the open end and a portion of the lead wire extending outward from the open end; and
a gripping member that grips a portion covered with the tube in an outer peripheral surface of the cylindrical body such that the tube protrudes to a side opposite to the open end,
wherein on a side of the cylindrical body where the open end is formed,
one or more caulked portions are formed, each of the caulked portions including
two inclined portions in each of which a diameter of the cylindrical body continuously changes along an axial direction of the cylindrical body, and
a bottom portion disposed between the two inclined portions in the axial direction and having a constant diameter of the cylindrical body along the axial direction,
the gripping member grips an outer peripheral surface of the caulked portion closest to the open end in the axial direction among the one or more caulked portions, the outer peripheral surface being covered with the tube, and
in each of the two inclined portions included in the caulked portion gripped by the gripping member, (A) or (B) is 30° or more and less than 90°, where
(A) is an angle between the inclined portion and a plane obtained by extending the bottom portion toward a side of the inclined portion, and
(B) is an angle between a plane parallel to a tangent of the inclined portion at a contact point between the inclined portion and the bottom portion, and the plane obtained by extending the bottom portion toward the side of the inclined portion.
2. The gas sensor according to claim 1, wherein an axial length of the gripping member is equal to or less than an axial length of the caulked portion gripped by the gripping member.
3. The gas sensor according to claim 1, wherein a diameter of a portion of the cylindrical body where the caulked portion is not formed is larger by 0.5 mm or more than a diameter of the cylindrical body at the bottom portion of the caulked portion gripped by the gripping member.
4. The gas sensor according to claim 1, wherein an outer peripheral surface of the cylindrical body at the open end is subjected to round chamfering.
5. The gas sensor according to claim 2, wherein a diameter of a portion of the cylindrical body where the caulked portion is not formed is larger by 0.5 mm or more than a diameter of the cylindrical body at the bottom portion of the caulked portion gripped by the gripping member.
6. The gas sensor according to claim 2, wherein an outer peripheral surface of the cylindrical body at the open end is subjected to round chamfering.

* * * * *